US008209196B2

United States Patent
Ariyoshi et al.

(10) Patent No.: US 8,209,196 B2
(45) Date of Patent: Jun. 26, 2012

(54) SPECIMEN TESTING APPARATUS, TEST INFORMATION MANAGEMENT APPARATUS, AND TEST INFORMATION OUTPUT METHOD

(75) Inventors: Shunsuke Ariyoshi, Kobe (JP); Daigo Fukuma, Kobe (JP)

(73) Assignee: Sysmex Corporation, Kobe (JP)

( * ) Notice: Subject to any disclaimer, the term of this patent is extended or adjusted under 35 U.S.C. 154(b) by 173 days.

(21) Appl. No.: 12/848,670

(22) Filed: Aug. 2, 2010

(65) Prior Publication Data

US 2011/0035237 A1     Feb. 10, 2011

(30) Foreign Application Priority Data

Aug. 4, 2009   (JP) ................................. 2009-181693

(51) Int. Cl.
*G06F 19/00*     (2006.01)
(52) U.S. Cl. ............... 705/3; 705/2; 422/64; 435/287.3; 436/50; 702/20
(58) Field of Classification Search .................... 422/64; 435/287.3; 436/50; 702/20
See application file for complete search history.

(56) References Cited

U.S. PATENT DOCUMENTS

| | | | | |
|---|---|---|---|---|
| 7,641,855 | B2 * | 1/2010 | Farina et al. ..................... | 422/64 |
| 2006/0004526 | A1 * | 1/2006 | Hadd et al. ....................... | 702/20 |
| 2007/0238181 | A1 * | 10/2007 | Lamont et al. .................. | 436/50 |
| 2011/0124096 | A1 * | 5/2011 | Philipak et al. ............ | 435/287.3 |

FOREIGN PATENT DOCUMENTS

JP         2008-020309 A       1/2008

OTHER PUBLICATIONS

ProQuest search results.*

* cited by examiner

*Primary Examiner* — Dilek B Cobanoglu
(74) *Attorney, Agent, or Firm* — Brinks Hofer Gilson & Lione

(57) ABSTRACT

The information processing unit receives input of a user ID and a password when the operator carries out log-in, and executes user authentication process. When the log-in process is carried out by the user, the information processing unit outputs test results together with a patient attribute information including patient ID, name of the patient, attending physician, medical wards, comments regarding patient, and the like. When the log-in process is carried out by the maintenance technician, the information processing unit outputs the test result only.

16 Claims, 20 Drawing Sheets

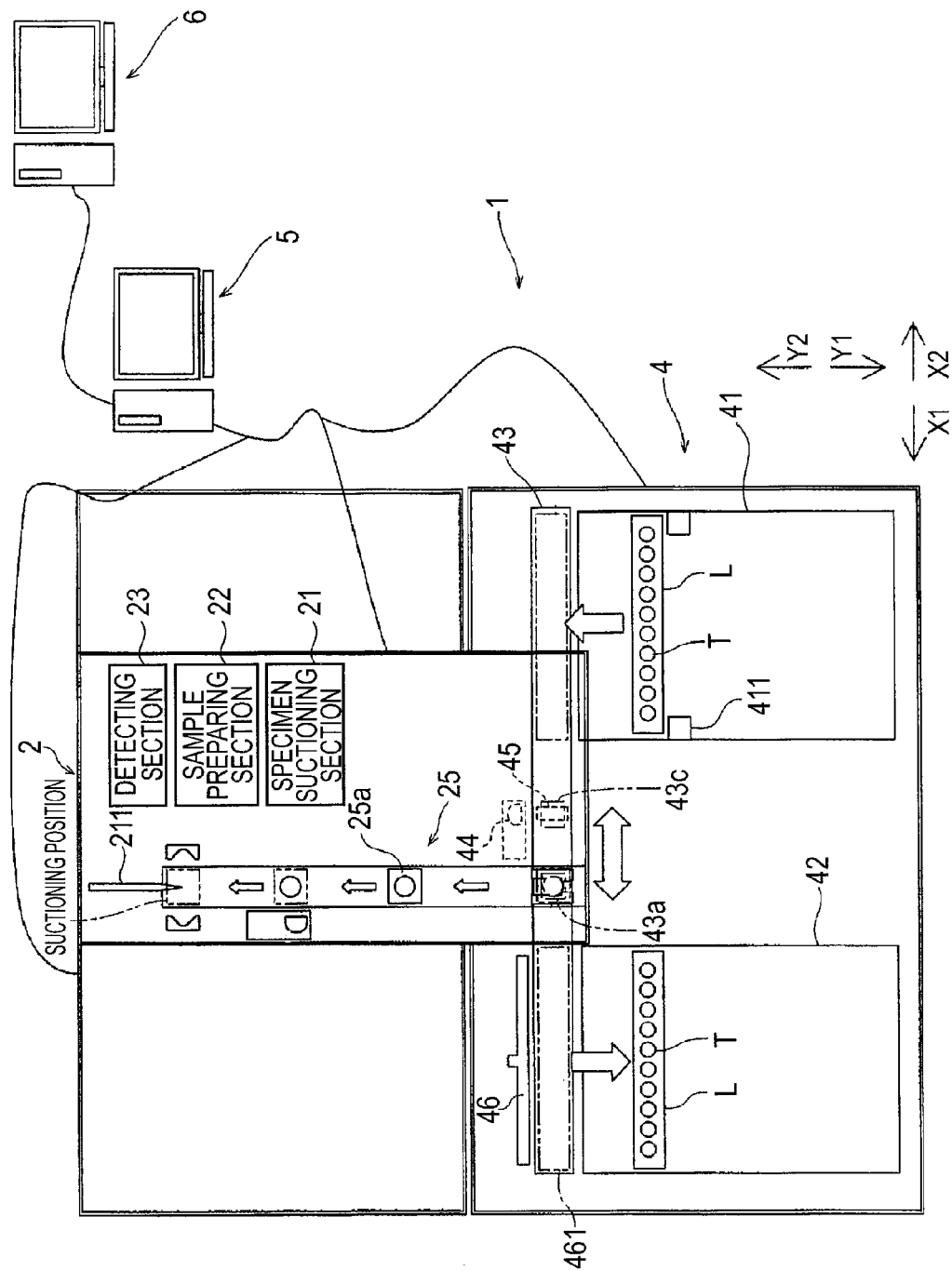

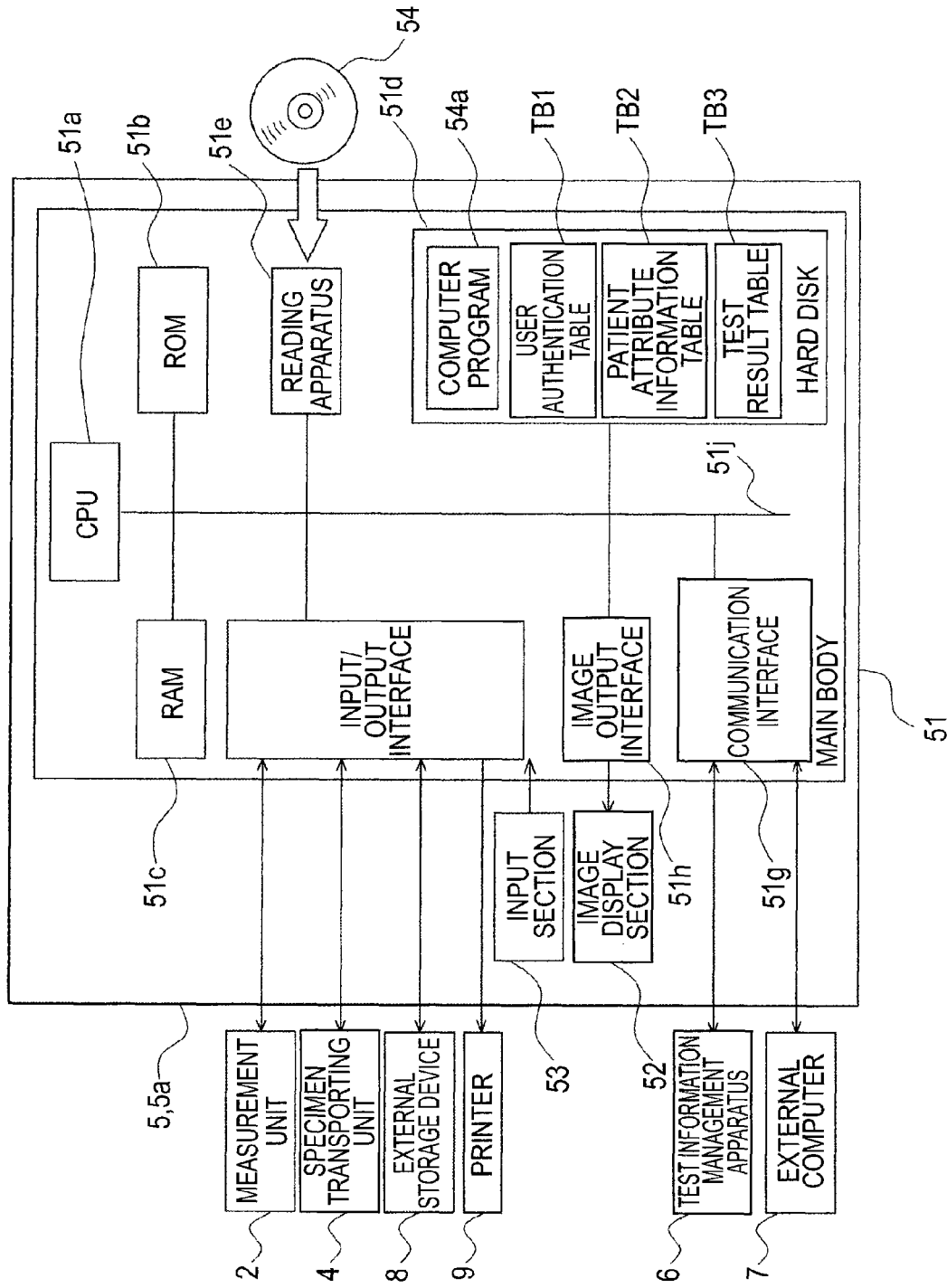

FIG.6B

| PATIENT ID | NAME | SEX | DATE OF BIRTH | MEDICAL WARDS | ATTENDING PHYSICIAN | COMMENTS REGARDING PATIENT |
|---|---|---|---|---|---|---|
| P01443 | JOHN PATENT | MALE | 1981/3/14 | 4A | SMITH | ○○ TENDENCY IS OBSERVED |
| U25817 | JANE UTILITY | FEMALE | 1995/7/21 | 3B | JACKSON | |
| D21431 | TOM DESIGN | MALE | 1969/10/3 | 6A | YOUNG | |
| ... | ... | ... | ... | ... | ... | |

TB2

F21, F22, F23, F24, F25, F26, F27

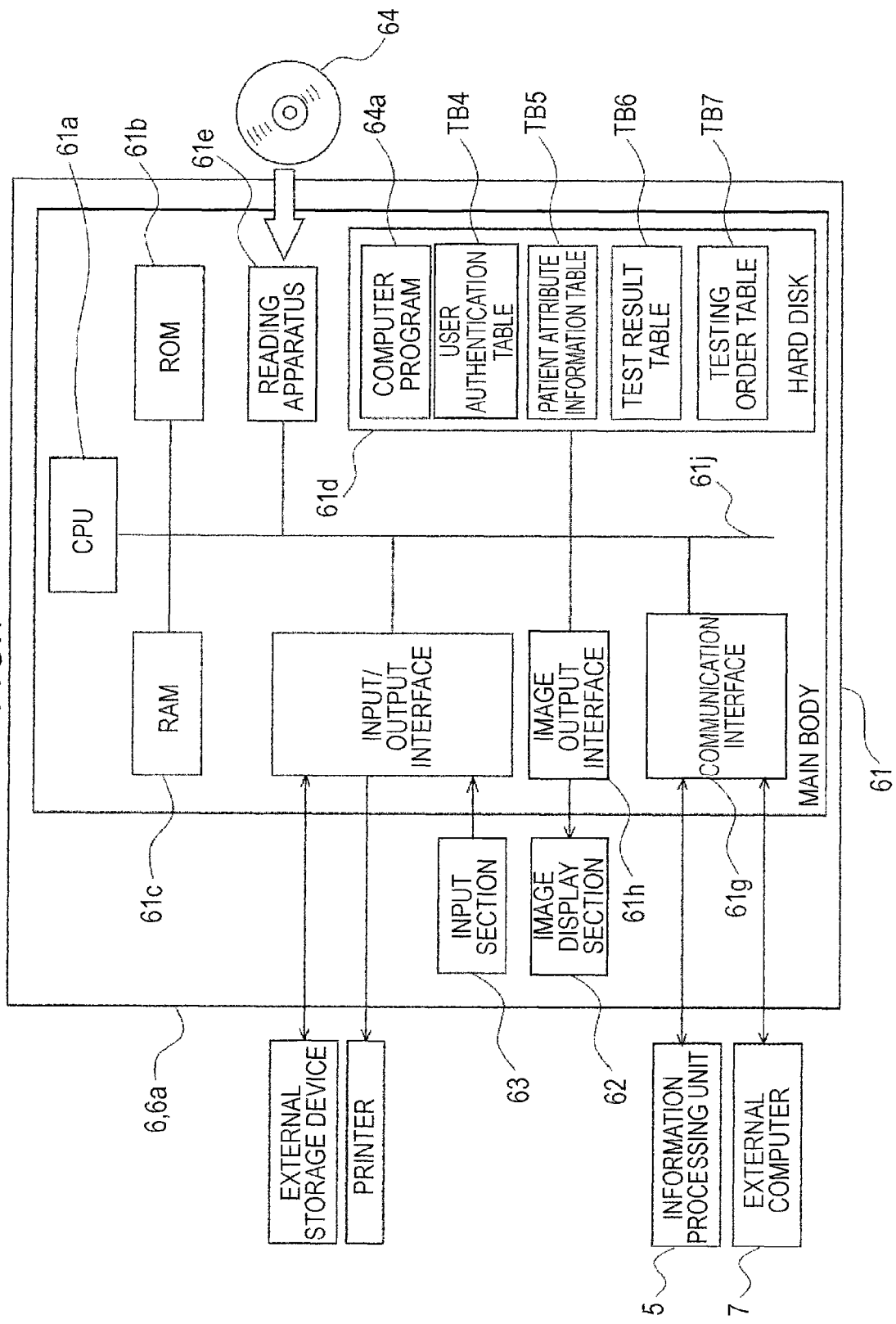

SPECIMEN TESTING APPARATUS, TEST INFORMATION MANAGEMENT APPARATUS, AND TEST INFORMATION OUTPUT METHOD

RELATED APPLICATIONS

This application claims priority under 35 U.S.C. §119 to Japanese Patent Application No. 2009-181693 filed on Aug. 4, 2009, the entire content of which is hereby incorporated by reference.

BACKGROUND OF THE INVENTION

1. Field of the Invention

The present invention relates to a specimen testing apparatus for testing a specimen collected from a subject, a test information management apparatus for managing information relating to a test, and a test information output method in the specimen testing apparatus.

2. Description of the Related Art

In an analyzing apparatus for analyzing clinical specimens, analysis results which were obtained by testing specimens collected from subjects and personal information such as names, which can specify each of the subjects, are stored. It is necessary to prevent the personal information, with which each of the subjects can be specified, from leaking externally in order to protect the personal information.

JP-laid open patent 2008-020309 discloses an analyzing system provided with an analyzing apparatus to be installed in a facility such as a hospital or the like and a management server installed outside the facility has been disclosed. JP-laid open patent 2008-020309 discloses a technique in which an analysis result is transmitted while keeping the personal information confidential at the time of transmitting the analysis result from the analyzing apparatus in the facility to the management server outside the facility has been disclosed.

SUMMARY OF THE INVENTION

The scope of the invention is defined solely by the appended claims, and is not affected to any degree by the statements within this summary.

A first aspect of present invention is a specimen testing apparatus comprising: a testing section for testing a specimen; a storage section for storing subject attribute information and test results in correspondence with each other, the subject attribute information comprising attribute information with which a subject from which the specimen has been collected can be specified, and the test results being obtained by testing the specimen collected from the subject relating to the subject attribute information by the testing section; an output section for outputting information stored in the storage section; and a controller, wherein the controller: receives input of the subject attribute information; controls the testing section such that the testing section tests the specimen and obtains the test results; causes the storage section to store the subject attribute information and the test results of the specimen collected from the subject relating to the subject attribute information in correspondence with each other; receives from an operator, identification information for identifying the operator; and controls the output section to output first test information comprising the subject attribute information and the test results relating to the subject attribute information when the received identification information corresponds to first type information which indicates that the operator belongs to the first type, and controls the output section to output second test information comprising not the attribute information, with which the subject can be specified, from among the subject attribute information, but the test results relating to the subject attribute information when the received identification information corresponds to second type information which indicates that the operator belongs to the second type.

A second aspect of present invention is a specimen testing apparatus comprising: a testing section for testing a specimen; and a controller, including a storage section under control of a processor, the storage section storing instructions enabling the processor to carry out operations, comprising: a step of receiving an input of subject attribute information including attribute information with which a subject from which the specimen has been corrected can be specified; a step of obtaining test results by testing the specimen by the testing section; a step of storing in the storage section the subject attribute information and the test results of the specimen collected from the subject relating to the subject attribute information in correspondence with each other; a step of receiving from an operator, identification information for identifying the operator; a first output step of outputting first test information comprising the subject attribute information stored in the storage section and the test results relating to the subject attribute information when the received identification information corresponds to first type information which indicates that the operator belongs to a first type; and a second output step of outputting second test information comprising not the attribute information with which a subject can be specified from among the subject attribute information stored in the storage section, but the test results relating to the subject attribute information when the received identification information corresponds to second type information which indicates that the operator belongs to a second type.

A third aspect of present invention is a test information management apparatus comprising: a storage section for storing subject attribute information and test result of a specimen in correspondence with each other, the subject attribute information comprising attribute information with which a subject from which a specimen has been collected can be specified, and the test result being obtained from the specimen collected from the subject relating to the subject attribute information; an output section for outputting information stored in the storage section; and a controller; wherein the controller: receives from an operator an input of identification information relating to the operator; and causes the output section to output first test information comprising the subject attribute information stored in the storage section and the test results relating to the subject attribute information when the received identification information corresponds to first type information which indicates that the operator belongs to the first type, and causes the output section to output second test information comprising not the attribute information, with which the subject can be specified, from among the subject attribute information stored in the storage section, but the test results relating to the subject attribute information when the received identification information corresponds to second type information which indicates that the operator belongs to the second type.

A fourth aspect of present invention is a test information output method in a specimen testing apparatus for storing subject attribute information containing attribute information with which a subject from which a specimen has been collected can be specified and test results of the specimen collected from the subject specified by the subject attribute information, the method comprising: receiving input of identification information for identifying an operator of the specimen testing apparatus; outputting first test information comprising the subject attribute information and the test results relating to the subject attribute information when the received identification information corresponds to first type information which indicates that the operator belongs to first type; and outputting second test information comprising not the attribute information with which the subject can be specified from among the subject attribute information but the test results relating to the subject attribute information when the received identification information corresponds to second type information which indicates that the operator belongs to second type.

BRIEF DESCRIPTION OF THE DRAWINGS

FIG. 4 is a block diagram illustrating a configuration of a measurement unit according to the embodiment.

FIG. 5 is a block diagram illustrating a configuration of an information processing unit according to the embodiment.

FIG. 6B is a schematic diagram illustrating a configuration of a patient attribute information table.

FIG. 7 is a block diagram illustrating a configuration of a test information management apparatus according to the embodiment.

DETAILED DESCRIPTION OF THE PREFERRED EMBODIMENTS

Hereinafter, an embodiment of the specimen testing apparatus of the present invention will be described in detail with reference to the accompanying drawings.

This embodiment is for a specimen testing apparatus for storing patient attribute data indicating names, ages, sexes, and the like of patients whose specimens were collected correspondingly to test results of the specimens, storing user IDs of operators corresponding to type information indicating the types of the operators (a user or a maintenance technician), displaying both the patient attribute data and the test result when an operator whose type is a user logs in, and displaying the test result without displaying the patient attribute data when an operator whose type is a maintenance technician logs in.

In this specification, "a user" is a person who uses the specimen testing apparatus for testing on the daily basis in the facility where the specimen testing apparatus is installed. Specifically, a clinical laboratory technologist corresponds to the user.

In addition, in this specification, "a maintenance technician" means a person who visits the facility where the specimen testing apparatus is installed and executes checking and maintenance of the specimen testing apparatus.

Moreover, in this specification, "subject attribute information" is also referred to as "patient attribute data". The patient attribute data contains at least information of the attributes with which the patients can be specified. In this embodiment, "the information of the attributes with which the patients can be specified" means the names of the patients. In this embodiment, the patient attribute data contains sex, date of birth, a medical ward, an attending physician, comments by a physician regarding the patient, and the like for each patient in addition to the name of the patient.

[Configuration of Specimen Testing Apparatus]

Figure 1:
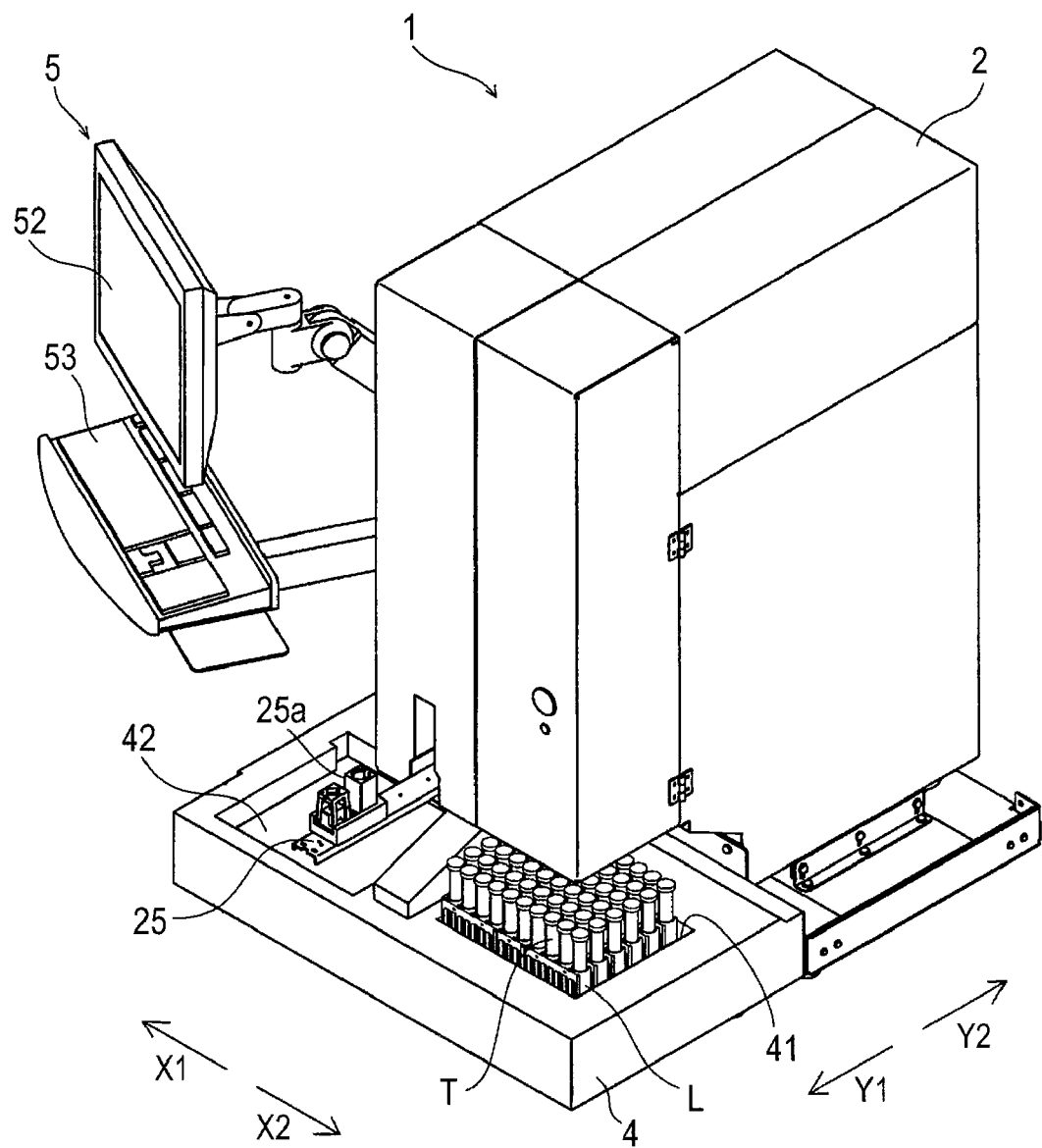
FIG. 1 is a perspective view illustrating an overall configuration of a specimen testing apparatus according to an embodiment.

FIG. 1 is a perspective view illustrating an overall configuration of a specimen testing apparatus according to this embodiment. A specimen testing apparatus 1 according to this embodiment is a multi-item blood cell analyzer for detecting blood cells such as white blood cells, red blood cells, blood platelets, and the like contained in a blood specimen and counting the number of each type of the blood cells. As shown in FIG. 1, the specimen testing apparatus 1 includes a measurement unit 2, a specimen transporting unit 4 arranged on the front surface side of the measurement unit 2, an information processing unit 5 capable of controlling the measurement unit 2 and the specimen transporting unit 4.

Figure 2:
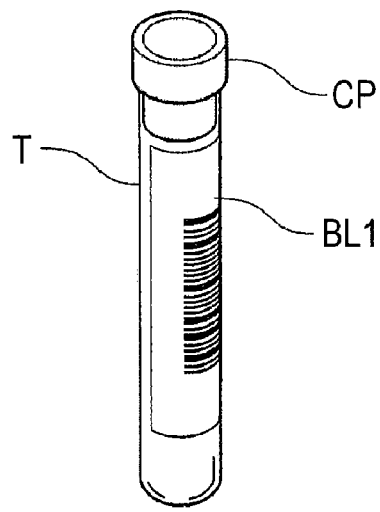
FIG. 2 is a perspective view illustrating an appearance of a specimen container.
Figure 3:
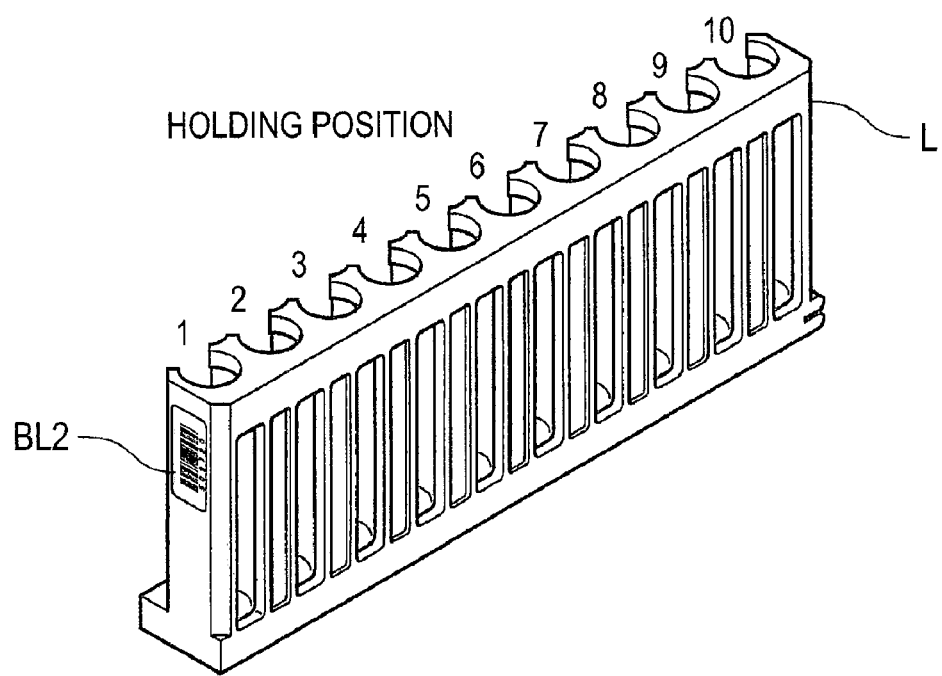
FIG. 3 is a perspective view illustrating an appearance of a sample rack.

FIG. 2 is a perspective view illustrating an appearance of a specimen container for containing a specimen, and FIG. 3 is a perspective view illustrating an appearance of a sample rack for holding a plurality of specimen containers. As shown in FIG. 2, the specimen container T has a tube shape, and the upper end thereof is opened. A blood specimen collected from a patient is contained inside, and the opening at the upper end is sealed with a cap section CP. The specimen container T is made of glass or synthetic resin having translucency, and the blood specimen therein is visible. In addition, a bar-code label BL1 is attached to the side surface of the specimen container T. A bar-code indicating a specimen ID is printed on the bar-code label BL1. Referring to FIG. 3, the sample rack L can align and hold 10 specimen containers T. Each specimen container T is held in a vertical state (upright position state) in the sample rack L. A bar-code label BL2 is attached to the side surface of the sample rack L. A bar-code indicating a rack ID is printed on the bar-code label BL2.

<Configuration of Measurement Unit>

FIG. 4 is a block diagram illustrating a configuration of a measurement unit. As shown in FIG. 4, the measurement unit 2 includes a specimen suctioning section 21 for suctioning blood as a specimen from the specimen container (blood collecting tube) T, a sample preparing section 22 for preparing a measurement sample to be used in the measurement of the blood constituents such as blood cells from the blood suctioned by the specimen suctioning section 21, and a detecting section 23 for detecting (measuring) blood cells from the measurement sample prepared by the sample preparing section 22. In addition, the measurement unit 2 further includes an introducing port (see FIG. 1) for introducing the specimen container T, which is contained in the sample rack L transported by a rack transporting section 43 of the specimen transporting unit 4, to the inside of the measurement unit 2, and a specimen container transporting section 25 for introducing the specimen container T from the sample rack L to the inside of the measurement unit 2 and transporting the specimen container T up to the suctioning position by the specimen suctioning section 21.

As shown in FIG. 4, the specimen suctioning section 21 is provided with a suctioning tube 211. In addition, the specimen suctioning section 21 can be moved in a perpendicular direction. The specimen suctioning section 21 is configured such that by causing the specimen suctioning section 21 to move downward, the suctioning tube 211 penetrates through the cap section CP of the specimen container T which has been transported up to the suctioning position, and the blood therein is suctioned.

The sample preparing section 22 is provided with a plurality of reaction chambers (not shown). In addition, the sample preparing section 22 is connected to a sample container which is not shown, and can supply reagent such as stain reagent, hemolytic agent, diluent, and the like to the reaction chambers. The sample preparing section 22 is also connected to the suctioning tube 211 of the specimen suctioning section 21, and can supply the blood specimen suctioned by the suctioning tube 211 to the reaction chambers. Such a sample preparing section 22 is for mixing and stirring the specimen and the reagent within the reaction chambers, and preparing a sample for measurement (measurement sample) by the detecting section 23.

The detecting section 23 can perform RBC (red blood cells) detection and PLT (blood platelets) detection in the sheath flow DC detecting method. In the RBC detection and the PLT detection in this sheath flow DC detecting method, a measurement of the measurement sample, which was obtained by mixing the specimen and the diluent, is performed, and numerical data of RBT and PLT are acquired by an analyzing process of the measurement data, which was thus obtained, by the information processing unit 5. In addition, the detecting section 23 can perform HGB (hemoglobin) detection in the SLS-hemoglobin method, and is configured to be able to perform the detection of WBC (white blood cells), NEUT (neutrophils), LYMPH (lymphocytes), EO (eosinophils), BASO (basocytes), and MONO (monocytes) in the flow cytometry method using a semiconductor laser. In this detecting section 23, numerical data of NEUT, LYMPH, EO, BASO, MONO, and WBC is acquired by an analyzing process of the measurement data, which was obtained by the measurement of the white blood cells, by the information processing unit 5.

The description will be made of the configuration of the specimen container transporting section 25. The specimen container transporting section 25 is provided with a hand section 25a capable of gripping the specimen container T. The hand section 25a includes a pair of gripping members which are arranged so as to be opposite each other, and can cause these gripping members to be closer to or to be separated from each other. The gripping members make it possible to grip the specimen container T. In addition, the specimen container transporting section 25 can move the hand section 25a in the vertical direction and in the back and forth direction (Y direction), and shake the hand section 25a. With such a configuration, it is possible to grip the specimen container T, which is contained in the sample rack L and positioned at a specimen supply position 43a, by the hand section 25a, pull out the specimen container T from the sample rack L by moving the hand section 25a upward in the state, and stir the specimen in the specimen container T by shaking the hand section 25a.

In addition, the specimen container transporting section 25 is provided with a specimen container setting section 25b with a hole section into which the specimen container T can be inserted. The specimen container T gripped by the above-mentioned hand section 25a is moved after being stirred, and the gripped specimen container T is inserted into the hole section of the specimen container setting section 25b. The specimen container setting section 25b can be moved to the suctioning position 21a by the specimen suctioning section 21. When the specimen container setting section 25b is moved up to the suctioning position, the specimen is suctioned from the set specimen container T by the specimen suctioning section 21.

<Configuration of Specimen Transporting Unit>

Next, the description will be made of the configuration of the specimen transporting unit 4. As shown in FIG. 1, the specimen transporting unit 4 is arranged in front of the measurement unit 2 of the specimen testing apparatus 1. Such a specimen transporting unit 4 can transport the sample rack L in order to supply the specimen to the measurement unit 2.

As shown in FIG. 4, the specimen transporting unit 4 includes a rack-before-analysis holding section 41 capable of temporarily holding a plurality of sample racks L which hold specimen containers T containing the specimens before analysis, a rack-after-analysis holding section 42 capable of temporarily holding a plurality of sample racks L which hold specimen containers T from which the specimens have been suctioned by the measurement unit 2, a rack transporting section 43 for linearly moving the sample rack L horizontally in the direction of an arrow X1 or X2 in the drawing and transporting the sample rack L received from the rack-before-analysis holding section 41 to the rack-after-analysis holding section 42 in order to supply the specimens to the measurement unit 2, a bar-code reading section 44, and a specimen container sensor 45 for detecting whether or not the specimen container T exists.

The rack-before-analysis holding section 41 has a square shape in a plan view, and the width thereof is slightly wider than that of the sample rack L. This rack-before-analysis holding section 41 is formed so as to be a little lower than the surface of the circumference, and the sample rack L before analysis is mounted on the upper surface thereof In addition, rack sending-in sections 41b are provided from both side surfaces of the rack-before-analysis holding section 41 so as to be able to protrude inwardly. The rack sending-in sections 41b engage with the sample rack L when protruding, and the sample rack L is sent backward (in a Y2 direction) when the rack sending-in sections 41*b* moves backward (in the Y2 direction) in this state. Such rack sending-in sections 41*b* are configured to be able to be driven by a stepping motor, which is not shown, provided below the rack-before-analysis holding section 41.

The rack transporting section 43 can send the sample rack L, which has been sent by the rack-before-analysis holding section 41, in the X1 or X2 direction by a belt. The specimen supply position 43*a* and the bar-code reading position 43*c* exist on the transport path of the sample rack L by the rack transporting section 43. The specimen supply position 43*a* is a position for supplying the specimens to the measurement unit 2 shown in FIG. 4, and the bar-code reading position 43*c* is a position where the bar-code reading section 44 reads the bar-code printed on the bar-code label BL1 of the specimen container T.

The bar-code reading section 44 is configured to read the bar-code printed on the bar-code label BL1 of the specimen container T shown in FIG. 2, and read the bar-code printed on the bar-code label BL2 attached to the sample rack L. The bar-code printed on the bar-code label BL2 of the sample rack L is attached so as to be unique to each rack, and is used for the management of the specimen analysis results. The bar-code reading position 43*c* is provided on the side of the X2 direction from the above-mentioned specimen supply position 43*a* on the transport path of the sample rack L by the rack transporting section 43, and the bar-code reading section 44 as described above is positioned near the bar-code reading position 43*c*. With such a configuration, the bar-code reading section 44 can read the specimen bar-code in the specimen container T positioned at the bar-code reading position 43*c*.

In addition, the specimen transporting unit 4 is controlled by the information processing unit 5, and supplies the specimen to the measurement unit 2 by causing the hand section 25*a* of the measurement unit 2 to grip the transported specimen container T and pulling out the specimen container T from the sample rack L when the specimen is transported to the specimen supply position 43*a*. The hand section 25*a* gripping the specimen container T in this manner enters into the case of the measurement unit 2 as described above, and thereby the specimen is introduced into the measurement unit 2.

The specimen container sensor 45 is a contact type sensor, and includes a contact piece which is constituted by a flexible member, a light emitting element which emits light, and a light receiving element (not shown). The specimen container sensor 45 is configured to be bent when the contact piece abuts on a detected object as a detection target, and as a result, the light emitted from the light emitting element is reflected by the contact piece and then incident to the light receiving element. With such a configuration, the contact piece is bent by the specimen container T when the specimen container T as a detection target, which is contained in the sample rack L, passes below the specimen container sensor 45. Thus, the specimen container T can be detected. The specimen container sensor 45 is provided at the bar-code reading position 43*c*. With such a configuration, it is possible for the specimen container sensor 45 to detect whether or not the specimen container T exists at the bar-code reading position 43*c*.

The rack-after-analysis holding section 42, which will be described later, is provided at the end on the downstream side in the transport direction of the rack transporting section 43, and the rack sending-out section 46 is provided at the back of the rack-after-analysis holding section 42. Such a rack sending-out section 46 is configured to be linearly moved horizontally in the direction of an arrow Y1 by the driving force of the stepping motor which is not shown. With such a configuration, it is possible to push and move the sample rack L into the rack-after-analysis holding section 42 by moving the rack sending-out section 46 in the Y2 direction when the sample rack L is transported to a position 461 (hereinafter, referred to as a "rack-after-analysis sending-out position") between the rack-after-analysis holding section 42 and the rack sending-out section 46.

The rack-after-analysis holding section 42 has a square shape in a plan view, and the width thereof is slightly wider than that of the sample rack L. This rack-after-analysis holding section 42 is formed so as to be a little lower than the surface of the circumference, and the sample rack L after analysis is mounted on the upper surface thereof. The rack-after-analysis holding section 42 is provided continuously to the above-mentioned rack transporting section 43, and is configured such that the sample rack L is sent in from the rack transporting unit 43 by the rack sending-out section 46 as described above.

With the above-mentioned configuration, the specimen transporting unit 4 can transport the sample rack L, which is mounted on the rack-before-analysis holding section 41, to the rack transporting section 43, and cause the rack transporting unit 43 to transport the specimen to the bar-code reading position 43*c*, detect whether or not the specimen container exists, read the specimen ID, further transport the specimen, whose specimen ID has been read, to the first specimen supply position 43*a* or a second specimen supply position 43*b*, and supply the specimen to the measurement unit 2 or a second measurement unit 3. In addition, the sample rack L containing the specimen, for which the suctioning has been completed, is transported to the rack-after-analysis sending-out position 461 by the rack transporting section 43, and sent out to the rack-after-analysis holding section 42 by the rack sending-out section 46. When a plurality of sample racks L is mounted on the rack-before-analysis holding section 41, the sample racks L containing the specimens, for each of which the suctioning has been completed, are sequentially sent out to the rack-after-analysis holding section 42 by the rack sending-out section 46, and the plurality of sample racks L are stocked in the rack-after-analysis holding rack 42.

<Configuration of Information Processing Unit>

Next, the description will be made of the configuration of the information processing unit 5. The information processing unit 5 is constituted by a computer. FIG. 5 is a block diagram illustrating a configuration of the information processing unit 5. The information processing unit 5 is implemented by a computer 5*a*. As shown in FIG. 5, the computer 5*a* includes a main body 51, an image display section 52, an input section 53. The main body 51 includes a CPU 51*a*, a ROM 51*b*, a RAM 51*c*, a hard disk 51*d*, a reading apparatus 51*e*, an input/output interface 51*f*, a communication interface 51*g*, and an image output interface 51*h*. The CPU 51*a*, the ROM 51*b*, the RAM 51*c*, the hard disk 51*d*, the reading apparatus 51*e*, the input/output interface 51*f*, the communication interface 51*g*, and the image output interface 51*h* are connected by a bus 51*j*.

The CPU 51*a* can execute a computer program loaded in the RAM 51*c*. The computer 5*a* functions as the information processing unit 5 when the CPU 51*a* executes a computer program 54*a* for the specimen analysis or for the control of the measurement unit 2 and the specimen transporting unit 4, which will be described later.

The ROM 51*b* is constituted by a mask ROM, a PROM, an EPROM, an EEPROM or the like, and records a computer program to be executed by the CPU 51*a*, data and the like to be used for this computer program.

The RAM 51c is constituted by an SRAM, a DRAM, or the like. The RAM 51c is used for reading the computer program 54a recorded in the hard disk 51d. In addition, the RAM 51c is used as a work area of the CPU 51a when the CPU 51a executes the computer program.

Various computer programs such as an operating system, an application program, and the like to be executed by the CPU 51a and data used for executing the computer programs are installed in the hard disk 51d. The computer program 54a, which will be described later, is also installed in this hard disk 51d.

The reading apparatus 51e is constituted by a flexible disk drive, a CD-ROM drive, a DVD-ROM drive, or the like, and can read the computer program or the data recorded in a portable recording medium 54. In addition, the computer program 54a for causing the computer to function as the information processing unit 5 is stored in the portable recording medium 54, and the computer 5a can read the computer program 54a from the portable recording medium 54 and install the computer program 54a to the hard disk 51d.

The computer program 54a can be provided not only by the portable recording medium 54 but also from an external device, which is connected to the computer 5a so as to be able to communicate with the computer 5a by an electric communication line (wired or wireless), through the electric communication line. For example, it is also possible that the computer program 54a is stored in a hard disk of a server computer on the internet, and the computer 5a accesses this server computer to download the computer program and installs this in the hard disk 51d.

In addition, a multi task operating system such as Windows (registered trademark) manufactured and distributed by Microsoft Corporation in the USA or the like is installed in the hard disk 51d. In the following description, the computer program 54a according to this embodiment is assumed to operate on the operating system.

Figure 6A:
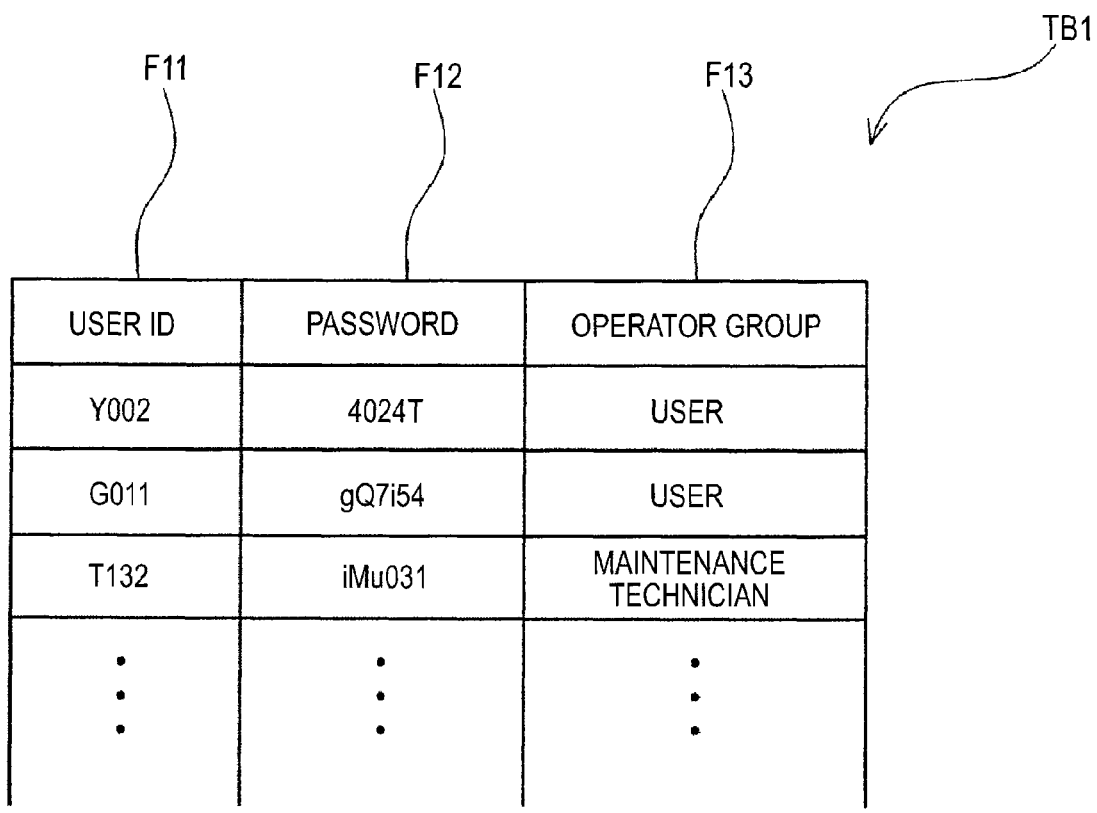
FIG. 6A is a schematic diagram illustrating a configuration of a user authentication table.
Figure 6C:
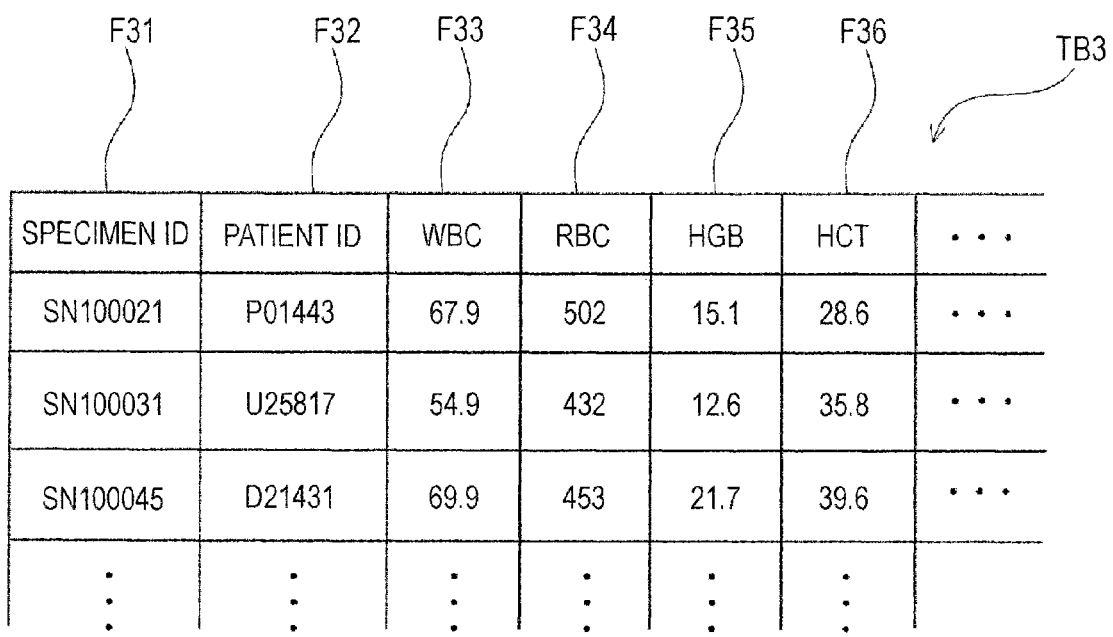
FIG. 6C is a schematic diagram illustrating a configuration of a test result table.

In addition, a user authentication table TB1, a patient attribute information table TB2, and a test result table TB3 are provided in the hard disk 51d. FIG. 6A is a schematic diagram illustrating a configuration of the user authentication table TB1, FIG. 6B is a schematic diagram illustrating a configuration of the patient attribute information table TB2, and FIG. 6C is a schematic diagram illustrating a configuration of the test result table TB3. As shown in FIG. 6A, the user authentication table TB1 is a table including a field F11 for user IDs, a field F12 for passwords, and a field F13 for user groups. That is, the user authentication table TB1 stores the information of the user IDs, the passwords, and the user groups while making a correspondence between them. As user groups, "user" as a group for general users and "maintenance technician" as a group for maintenance technicians exist. When user information of an operator is to be registered, a user ID, a password, and a user group ("user" or "maintenance technician") are designated, and thereby a record including such information is registered in the user authentication table TB1. Such a user authentication table TB1 is used in the user authentication, which will be described later.

The patient attribute information table TB2 is a table including a field F21 for patient IDs, a field F22 for names, a field F23 for sexes, a field F24 for dates of birth, a field F25 for medical wards, a field F26 for attending physicians, and a field F27 for comments regarding patients. That is, the patient attribute information table TB2 stores the patient IDs, the names, the sexes, the dates of birth, the medical wards to which the patients belong, the attending physicians of the patients, and the comments by the attending physicians regarding patients while making a correspondence between them.

The test result table TB3 is a table including a plurality of fields such as a field F31 for specimen IDs, a field F32 for patient IDs, a field F33 for WBC, a field F34 for RBC, a field F35 for HGB (hemoglobin), a field F36 for HCT (hematocrit), and the like. That is, the test result table TB3 stores the specimen IDs, the patient IDs, and various pieces of information regarding test results of RBC, PLT, and the like while making corresponding relationships therebetween.

As described above, the fields F21 and F32 for patient IDs are provided in common in the patient attribute information table TB2 and in the test result table TB3. Accordingly, the patient attribute information stored in the patient attribute information table TB2 and the test results stored in the test result table TB3 are linked by the common patient IDs, and a correspondence is made between them. For example, patient attribute information in the first row in the patient attribute information table TB2 shown in FIG. 6B (patient ID "P01443", name "John Patent", sex "male", date of birth "Mar. 14, 1981", medical ward "4A", attending physician "Smith", comment regarding patient "xx tendency is observed") and the test results with the common patient ID "P01443" in the first row in the test result table TB3 shown in FIG. 6C (specimen ID "SN100021", patient ID "P01443", WBC "67.9", RBC "502", HGB "15.1", HCT "28.6", . . . ) are stored in the hard disk 51d while making a correspondence between them.

The input/output interface 51f is constituted by a serial interface such as USB, IEEE1394, RS-232C, or the like, a parallel interface such as SCSI, IDE, IEEE1284, or the like, and an analog interface such as a D/A converter, an A/D converter, or the like. An input section 53 constituted by a keyboard and a mouse is connected to the input/output interface 51f, and it is possible to input data to the computer 5a when the user uses the input section 53. In addition, the input/output interface 51f is connected to the measurement unit 2 and the specimen transporting unit 4. With this configuration, the information processing unit 5 can control the measurement unit 2 and the specimen transporting unit 4, respectively.

In addition, an external storage device 8 such as a USB memory, an external hard disk, or the like can be connected to the input/output interface 51f, and the input/output interface 51f can read/write data from/on the connected external storage device 8. Moreover, a printer 9 can be connected to the input/output interface 51f. With such a configuration, it is possible to print the information displayed on the image display section 52 using the printer 9 when the operator gives an instruction for printing from the input section 53.

The communication interface 51g is Ethernet (registered trademark) interface. The communication interface 51g is connected to a test information management apparatus 6 and a management server 7 via a LAN. The computer 5a can exchange data with the test information management apparatus 6 and the external computer 7, which are connected to the LAN, by using a predetermined communication protocol by the communication interface 51g.

The image output interface 51h is connected to the image display section 52 constituted by an LCD, a CRT, or the like, and is configured to output a video signal in accordance with the image data supplied from the CPU 51a, to the image display section 52. The image display section 52 displays the image (screen) based on the input video signal.

<Configuration of Test Information Management Apparatus>

The test information management apparatus 6 is an apparatus which is disposed in a facility to manage the information regarding the test, a so-called LIS (Laboratory Information System), and is connected not only to the specimen testing apparatus 1 but also to the other specimen testing apparatuses. Such a test information management apparatus 6 receives the patient attribute information and testing orders for the patients, which are input from the operator or transmitted from other apparatuses such as an electronic medical recording system and the like, and stores and manages the information. Moreover, the test information management apparatus 6 receives an order request from the specimen testing apparatus 1, transmits the requested testing order and the patient attribute information regarding this testing order to the specimen testing apparatus 1, receives the test results from the specimen testing apparatus 1, and stores and manages the test results.

FIG. 7 is a block diagram illustrating a configuration of the test information management apparatus 6. The test information management apparatus 6 is implemented by a computer 6a. As shown in FIG. 7, the computer 6a includes a main body 61, an image display section 62, and an input section 63. The main body 61 includes a CPU 61a, a ROM 61b, a RAM 61c, a hard disk 61d, a reading apparatus 61e, an input/output interface 61f, a communication interface 61g, and an image output interface 61h. The CPU 61a, the ROM 61b, the RAM 61c, the hard disk 61d, the reading apparatus 61e, the input/output interface 61f, the communication interface 61g, and the image output interface 61h are connected via a bus 61j. When the CPU 61a executes a computer program 64a for the test information management, which will be described later, the computer 6a functions as the test information management apparatus 6. In addition, the configurations of the CPU 61a, the ROM 61b, the RAM 61c, the hard disk 61d, the reading apparatus 61e, the input/output interface 61f, the communication interface 61g, the image output interface 61h, the image display section 62, and the input section 63 are the same as those of the CPU 51a, the ROM 51b, the RAM 51c, the hard disk 51d, the reading apparatus 51e, the input/output interface 51f, the communication interface 51g, the image output interface 51h, the image display section 52, and the input section 53 of the information processing unit 5.

The computer program 64a for the test information management is installed in the hard disk 61d. In addition, a multi task operating system such as Windows (registered trademark) manufactured and distributed by Microsoft Corporation in the USA or the like is installed in the hard disk 61d. In the following description, the computer program 64a according to this embodiment is assumed to operate on the operating system.

The computer program 64a for causing the computer to function as the test information management apparatus 6 is stored in the portable recording medium 64, and the computer 6a can read the computer program 64a from the portable recording medium 64 to install the computer program 64a in the hard disk 61d.

The computer program 64a can be provided not only by the portable recording medium 64 but also from an external device, which is connected to the computer 6a so as to be able to communicate with the computer 6a by an electric communication line (wired or wireless), through the electric communication line. For example, it is also possible that the computer program 64a is stored in a hard disk of a server computer on the internet, and the computer 6a accesses this server computer to download the computer program and installs this in the hard disk 61d.

In addition, a user authentication table TB4, a patient attribute information table TB5, a test result table TB6, and a testing order table TB7 are provided in the hard disk 61d. Since the user authentication table TB4, the patient attribute information table TB5, and the test result table TB6 are the tables with the same structures as the user authentication table TB1, the patient attribute information table TB2, and the test result table TB3, each of which were described above, the description thereof will be omitted. The testing order table TB7 is a table in which corresponding relationships are made for the specimen ID, the patient attribute information for the patient who corresponds to the specimen ID, and the test items (measurement items) to be performed.

An input section 63 constituted by a keyboard and a mouse is connected to the input/output interface 61f. The communication interface 61g is connected to the information processing unit 5 via a LAN. The computer 6a can use the communication interface 61g to exchange data with the information processing unit 5, which is connected to the LAN, by using a predetermined communication protocol. In addition, the image display section 62 constituted by the LCD, the CRT, or the like is connected to the image output interface 61h.

[Operations of Specimen Testing Apparatus 1]

Hereinafter, the description will be made of the operations of the specimen testing apparatus 1 according to this embodiment.

The patient attribute information such as the patients' names, ages, sexes, and the like are input by the operator or transmitted from another apparatus, and provided to the test information management apparatus 6. The test information management apparatus 6 registers the received patient attribute information in the patient attribute information table TB5. With such a configuration, the patient attribute information is stored in the test information management apparatus 6.

In addition, when a specimen is collected from a patient, a specimen ID is allocated to the specimen, the testing order constituted by this specimen ID and test items is input by an operator or transmitted from another apparatus, and given to the test information management apparatus 6. The test information management apparatus 6 registers the received testing order in the testing order table TB7. With such a configuration, the testing order is stored in the test information management apparatus 6.

<Log-In Process>

Figure 8:
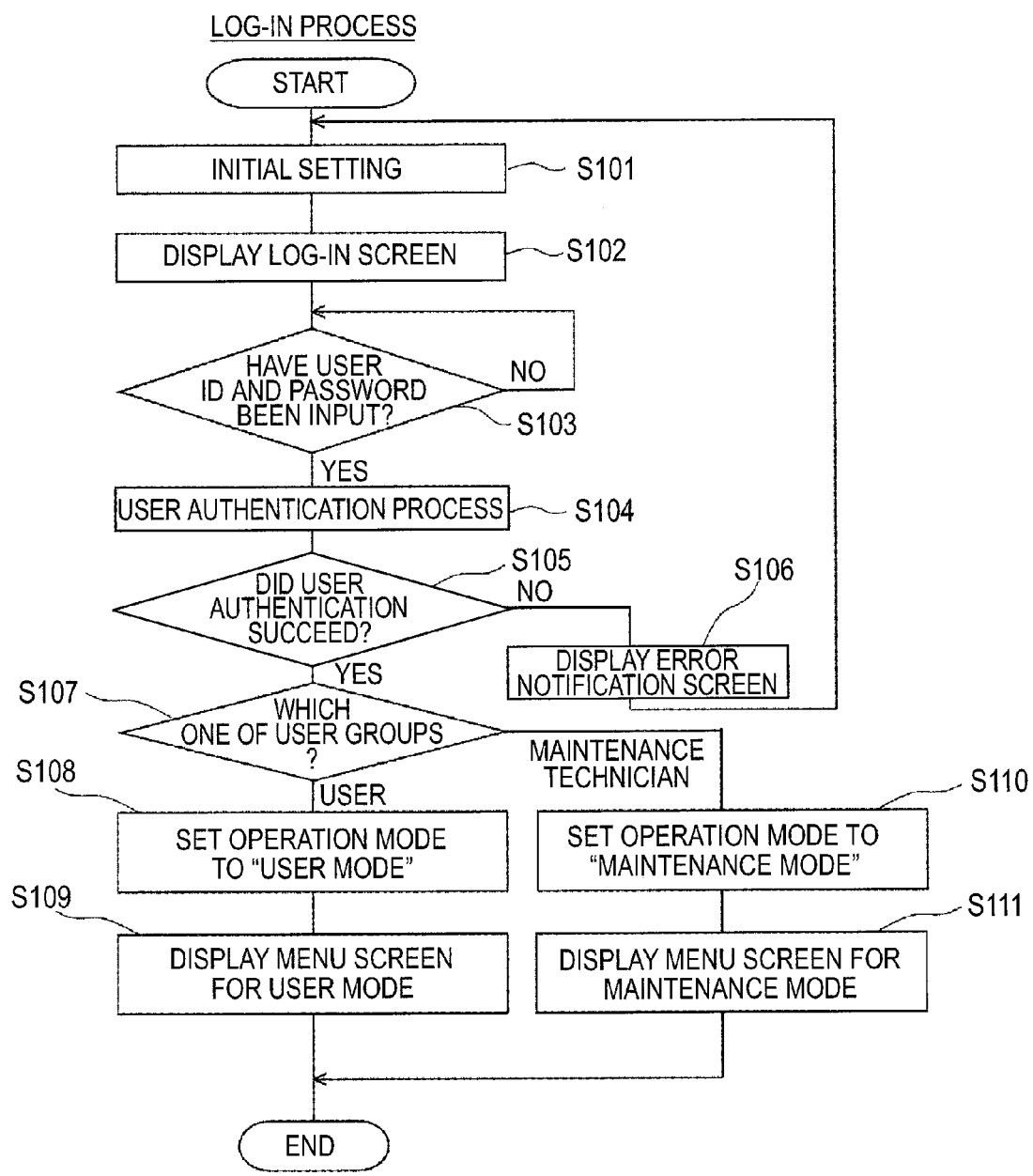
FIG. 8 is a flow chart illustrating a flow of a log-in process by an information processing unit of a specimen testing apparatus according to the embodiment.

FIG. 8 is a flow chart illustrating a flow of a log-in process by the information processing unit 5 of the specimen testing apparatus 1. When the computer 5a is started, and the execution command of the computer program 54a is given from an operator to the computer 5a, the CPU 51a executes an initial setting of the program 54a (step S101), and displays a log-in screen on the image display section 52 (step S102). Input boxes for inputting a user ID and a password are respectively provided on the log-in screen, and the operator inputs his/her own user ID and password to the information processing unit 5 using the input section 53. The CPU 51a waits for the input of the user ID and the password (NO in the step S103), and executes a user authentication process (step S104) when it receives the input of the user ID and the password (YES in step S103).

In the user authentication process, the CPU 51a checks the input user ID and the password with the user ID and the password registered in the user authentication table TB1, and determines whether the input user ID and the password have been registered. When the user authentication fails (NO in step S105), the CPU 51a displays the screen for notifying the error in the user authentication (step S106), and then returns the process to step S102.

When the user authentication succeeds (YES in step S105), the CPU 51a confirms the operator group of the record, which contains the user ID and the password, in the user authentication table TB1, and determines whether the operator group is the "user" or the "maintenance technician" (step S107). When the operator group is the "user" (the "user" in step S107), the CPU 51a sets the operation mode of the specimen testing apparatus 1 to a "user mode" (step S108). The operators belonging to the "user" group are authorized to output the patient attribute information. That is, the "user mode" is an operation mode in which it is possible to output the patient attribute information by the specimen testing apparatus 1. When the setting of the "user mode" is completed, the CPU 51a displays a menu screen for the "user mode" on the image display section 52 (step S109), and terminates the process.

On the other hand, when the operator group is the "maintenance technician" (the "maintenance technician" in step S107), the CPU 51a sets the operation mode of the specimen testing apparatus 1 to a "maintenance mode" (step S110). The operators belonging to the "maintenance technician" group are not authorized to output the patient attribute information. That is, the "maintenance mode" is an operation mode to restrict the output of the patient attribute information in the specimen testing apparatus 1. When the setting of the "maintenance mode" is completed, the CPU 51a displays a menu screen for the "maintenance mode" on the image display section 52 (step S111), and terminates the process.

Figure 9:
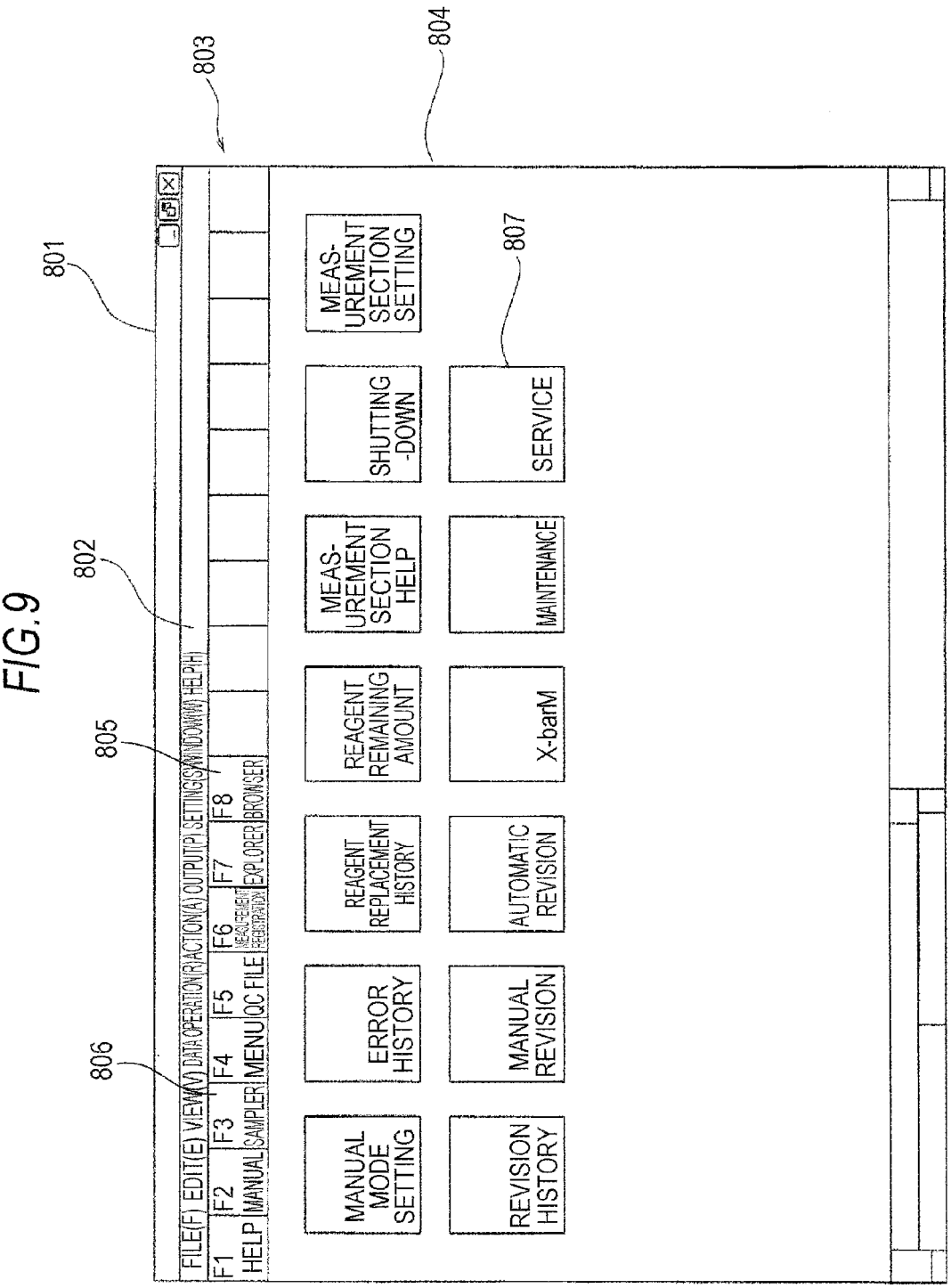
FIG. 9 is a diagram illustrating a screen configuration of a menu screen in a maintenance mode.

FIG. 9 is a diagram illustrating a screen configuration of a menu screen in the maintenance mode. All the screens (windows) displayed on the data processing unit 5 of the specimen testing apparatus 1 include a menu bar, a tool bar, and a work area, respectively. A menu bar 802, a tool bar 803, and a work area 804 are also provided in a menu screen 801.

In the menu bar 802, menus such as a "file", "edit", "view", and the like are provided, pull-down menus are displayed when the operator selects these menus by a click operation of the mouse or the like, and an operation corresponding to an item (such as a storage of the analysis results in the external storage device 8, a termination of the application, or the like) can be executed by selecting the desirable item from the pull-down menus. The contents common to this menu bar 802 (same menus) are also displayed in the screens other than the menu screen 801.

A plurality of icons is provided in the tool bar 803. The respective icons respectively correspond to the operations, which are often used, such as a display of a help screen, a manual measurement, a sampler measurement, a display of the menu screen, a display of a browser screen, and the like, and corresponding operations (commands) can be executed by selecting these icons by a click operation of the mouse or the like. This tool bar 803 includes a common icon which is displayed in common on the screens other than the menu screen 801 and an individual icon which is displayed individually on the respective screens. When an icon 805 included in the tool bar 803 is selected, the display command of the browser screen, which will be described later, will be executed, and the display is shifted to the browser screen. When an icon 806 is selected, a command for the specimen measurement is executed, and the measurement of the specimen is started. These icons 805 and 806 are common icons.

A plurality of icons is provided in the work area 804. The respective icons correspond to an error history screen, a maintenance screen on which it is possible to execute maintenance functions used in common by the users and the maintenance technicians, a maintenance screen on which it is possible to execute various maintenance functions for the maintenance technicians, and an operation for switching the display to a screen other than the menu screen. It is possible to execute the corresponding operation (command) by selecting these icons by a click operation of the mouse or the like. This work area 804 has different contents to be displayed on the screens other than the menu screen 801. In addition, the content of the work area 804 in the menu screen 801 in the maintenance mode is different from the one of the work area in the menu screen in the user mode. An icon 807 is a service icon for switching the display to the maintenance screen on which it is possible to execute various maintenance functions for the maintenance technician. This service icon 807 is an icon unique to the menu screen 801 in the maintenance mode, which is not displayed in the menu screen in the user mode.

<Specimen Measurement Process>

Figure 10A:
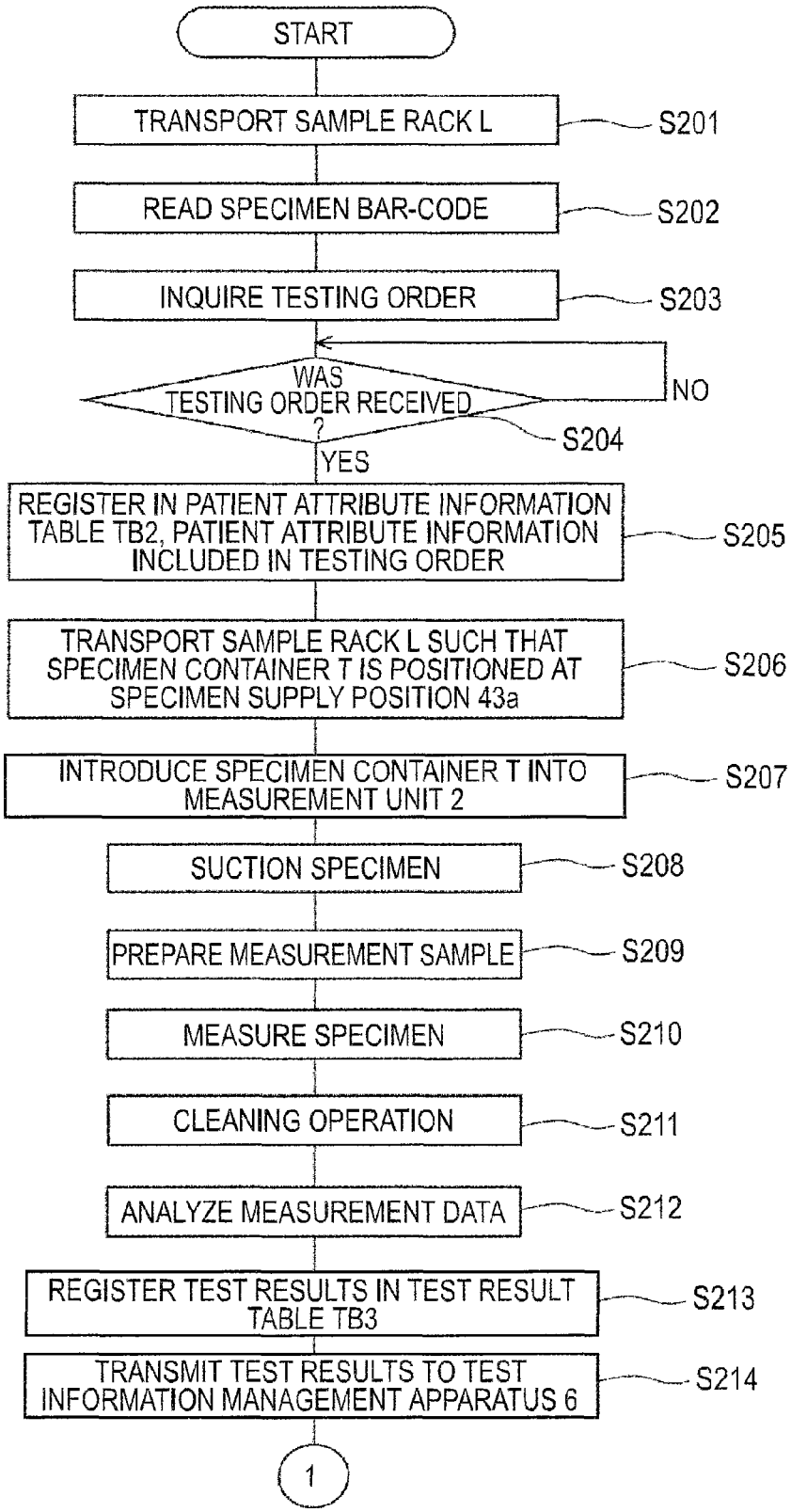
FIG. 10A is a flow chart illustrating a flow of a specimen measurement process by the information processing unit of the specimen testing apparatus according to the embodiment (first half part).
Figure 10B:
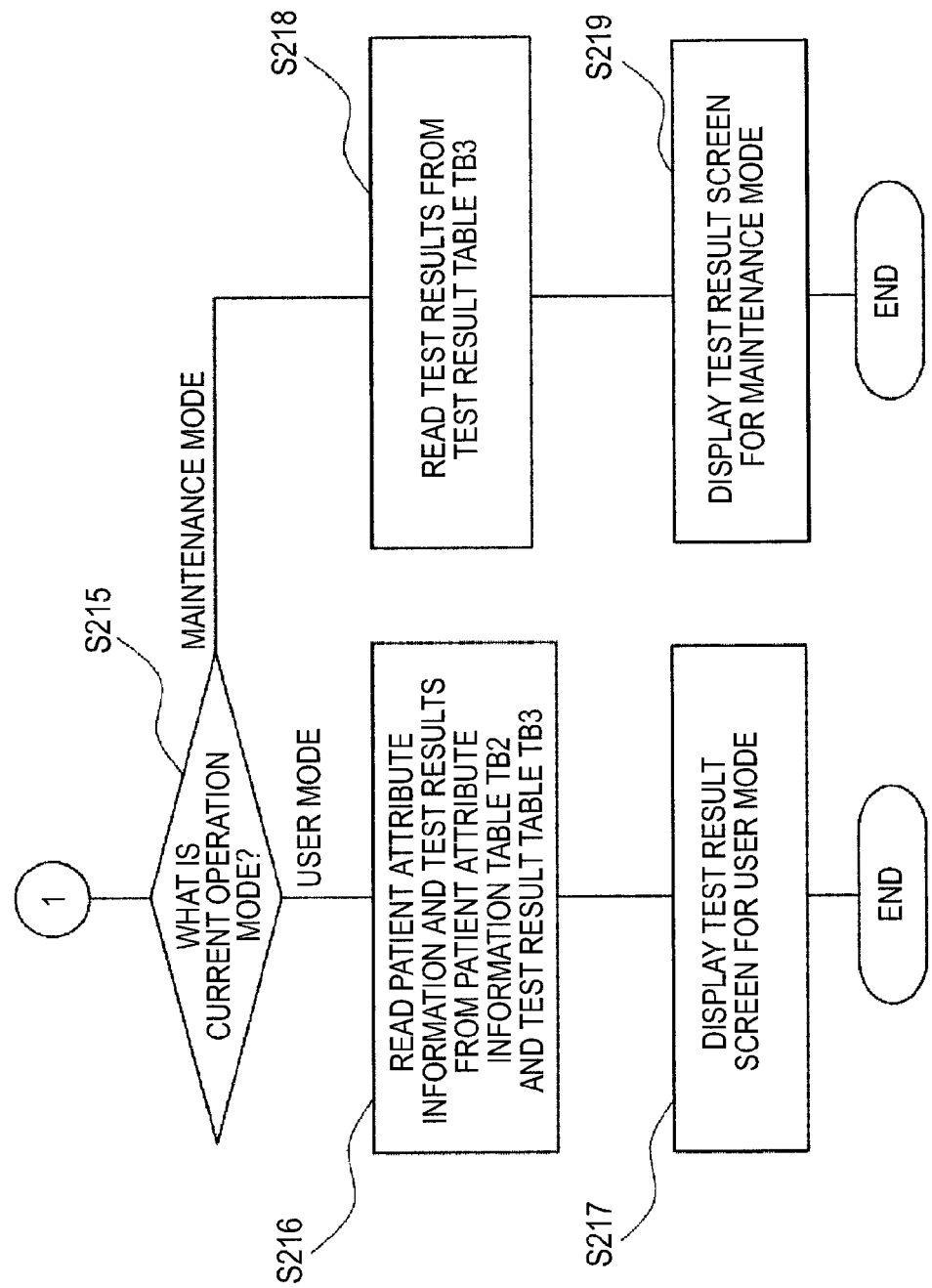
FIG. 10B is a flow chart illustrating a flow of the specimen measurement process by the information processing unit of the specimen testing apparatus according to the embodiment (second half part).

FIGS. 10A and 10B are flow charts illustrating the flows of the specimen measurement process by the information processing unit 5 of the specimen testing apparatus 1. The operator mounts a sample rack L holding a plurality of specimen container T containing specimens on the rack-before-analysis holding section 41. In this state, the operator operates the input section 53, and instructs the information processing unit 5 to execute the specimen measurement. When the CPU 51a of the information processing unit 5 receives the instruction for executing the specimen measurement and detects the sample rack L mounted on the rack-before-analysis holding section 41 by a sensor which is not shown, the CPU 51a executes the process in step S201.

In step S201, the CPU 51a controls the specimen transporting unit 4 to cause it to transport the sample rack L, and allows the specimen containers T held by the sample rack L to be positioned at the bar-code reading position 43c (step S201). Subsequently, the CPU 51a causes the bar-code reading section 44 to read a specimen ID from the specimen bar-code in the bar-code label BL1 of the respective specimen containers T (step S202).

The CPU 51a inquires of the test information management apparatus 6 about the testing order corresponding to the specimen ID read by the bar-code reading section 44 (step S203). This is executed by transmitting testing order request data including the specimen ID to the test information management apparatus 6 connected via the network.

When the test information management apparatus 6 receives the testing order request data, the test information management apparatus 6 searches the corresponding testing order from the testing order table TB7 while using as a key the specimen ID contained in the data. The patient attribute information regarding the patient, from whom the specimen was collected, is included in the thus obtained testing order. Such a testing order is transmitted from the test information management apparatus 6 to the information processing unit 5.

The CPU 51a of the information processing unit 5 waits for the reception of the testing order (NO in step S204). When the CPU 51a receives the testing order (YES in step S204), the CPU 51a stores the received testing order in the hard disk 51d and registers the patient attribute information contained in this testing order in the patient attribute information table TB2 (step S205).

The CPU 51a transports the sample rack L up to the position where the specimen container T is positioned at the specimen supply position 43a (step S206). Next, the CPU 51a controls the specimen container transporting section 25 of the measurement unit 2 to pull out the specimen container T from the sample rack L, introduces the specimen container T into the measurement unit 2, and transports the specimen container T to the suctioning position (step S207). Moreover, the CPU 51a controls the specimen suctioning section 21 to cause it to suction the specimen from the specimen container T by an amount necessary for the measurement (step S208), controls the sample preparing section 22 to prepare the sample for the measurement corresponding to the measurement items (step S209). The CPU 51a supplies the measurement sample to the detecting section 23 and causes the detecting section 23 to execute the measurement of the specimen regarding the respective measurement items contained in the testing order (step S210). With such operations, the CPU 51a obtains the measurement data output from the detecting section 23. Thereafter, the CPU 51a executes a cleaning operation for cleaning the flow passage, the reaction chamber, or the like used for the measurement (step S211).

The CPU 51a executes the analyzing process for the measurement data (step S212), and obtains the test results including numerical values of RBC, PLT, HGB, WBC, NEUT, LYMPH, EO, BASO, MONO, and the like. The CPU 51a registers the thus obtained test results in the test result table TB3 (step S213). In addition, the CPU 51a transmits the obtained test results to the test information management apparatus 6 along with the specimen ID (step S214). The transmitted test results are received by the test information management apparatus 6, and the CPU 61a of the test result information management apparatus 6 registers the received test results in the test result table TB6.

In addition, the CPU 51a determines which one of the user mode and the maintenance mode the current operation mode of the specimen testing apparatus 1 is in (step S215). When the current operation mode is in the user mode (the "user mode" in step S215), the CPU 51a reads the test results of the specimen from the test result table TB3, reads the patient attribute information, which contains the same patient ID as that in the test result, from the patient attribute information table TB2 (step S216), displays the test result screen for the "user mode" on the image display section 52 (step S217), and terminates the process. On the other hand, when the current operation mode is in the "maintenance mode" in step S215, the CPU 51a reads the test results of the specimen from the test result table TB3 (step S218), displays the test result screen for the "maintenance mode" on the image display section 52 (step S219), and terminates the process. The specimen measurement process as described above is repeatedly performed until the tests for all the specimens contained in the sample rack L are completed.

Figure 11:
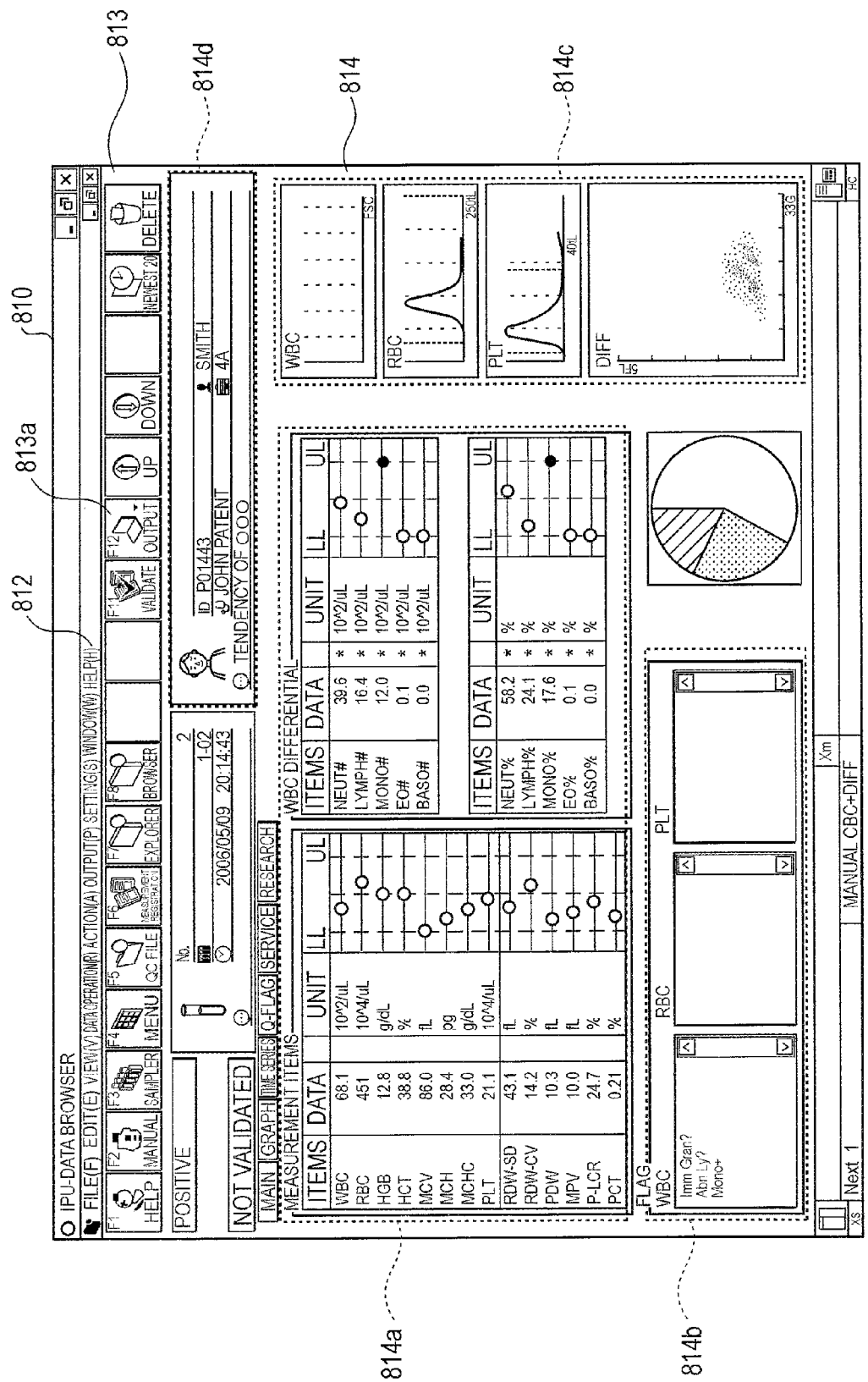
FIG. 11 is a diagram illustrating an example of a test result screen in a user mode.

FIG. 11 is a diagram illustrating an example of the test result screen in the user mode. A menu bar 812, a tool bar 813, and a work area 814 are provided in the test result screen 810. Various types of information regarding the test results are displayed in the work area 814. Specifically, an analysis result display part 814a, a flag display part 814b, and a particle size distribution diagram display part 814c are provided in the work area 814. The numerical value data of the test items such as WBC, RBC, HGB, and the like is displayed in a list form in the analysis result display part 814a. In addition, when there is an abnormality in the test result of the specimen, information indicating the abnormality and the like is displayed in the flag display part 814b. Histograms of RBC and PLT and scattergrams of 5-part differential of WBC (NEUT, LYMPH, EO, BASO, MONO) are displayed in the particle size distribution diagram display part 814c.

Moreover, a patient attribute information display part 814d is provided in the work area 814. The patient attribute information (the patient ID, the patient's name, the attending physician, the medical ward, the comments regarding the patient) is displayed in this patient attribute information display part 814d.

A "data operation" menu is provided in the menu bar 812, pull-down menus are displayed by selecting this "data operation" menu by a click operation of the mouse or the like, and the operator can instruct the specimen testing apparatus 1 to store the test results and the patient attribute information, which are displayed in the work area 814, in the external storage device 8 connected to the input/output interface 51f by selecting a "backup" item included in the pull-down menus.

An "output" icon 813a as an individual icon is included in the tool bar 813. The operator can instruct to print the test results and the patient attribute information, which are displayed in the work area 814, by a printer 9 connected to the input/output interface 51f, or instruct to transmit them to the external computer 7 connected via the network, by selecting the icon 813a by a click operation of the mouse or the like.

Figure 12:
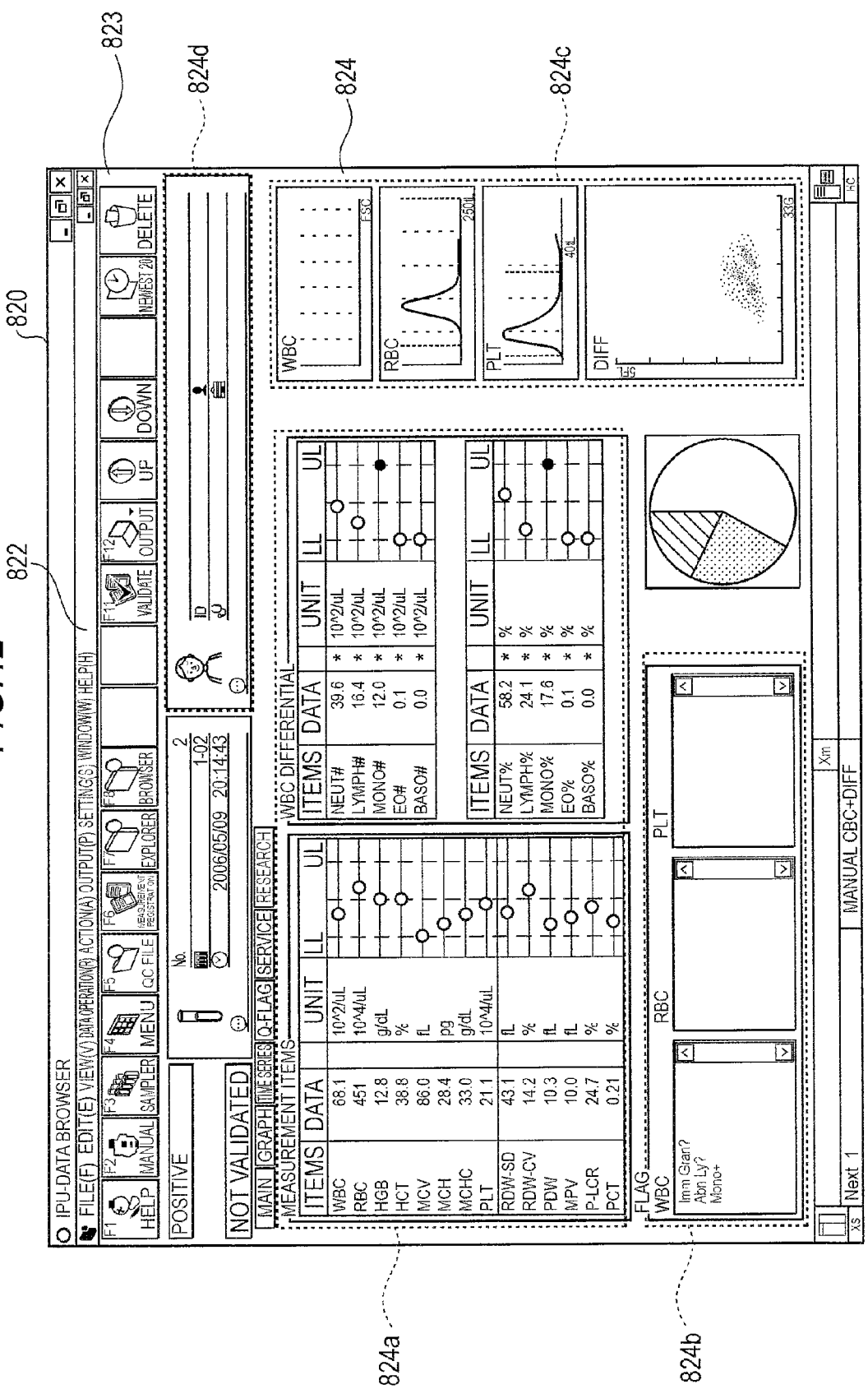
FIG. 12 is a diagram illustrating an example of the test result screen in a maintenance mode.

FIG. 12 is a diagram illustrating an example of the test result screen in the maintenance mode. A menu bar 822, a tool bar 823, and a work area 824 are provided in the test result screen 820 for the maintenance mode. The menu bar 822 and the tool bar 823 are the same as the menu bar 812 and the tool bar 813 in the test result screen 810 in the user mode.

An analysis result display part 824a, a flag display part 824b, and a particle size distribution diagram display part 824c are provided in the work area 824, and these are the same as the analysis result display part 814a, the flag display part 814b, and the particle size distribution diagram display part 814c in the test result screen 810 for the user mode. On the other hand, the patient attribute information is not displayed in the patient attribute information display part 824d in the test result screen 820 for the maintenance mode. With such a configuration, it is possible to prevent the maintenance technicians from viewing the patient attribute information.

<Test Result Display Process>

Figure 13:
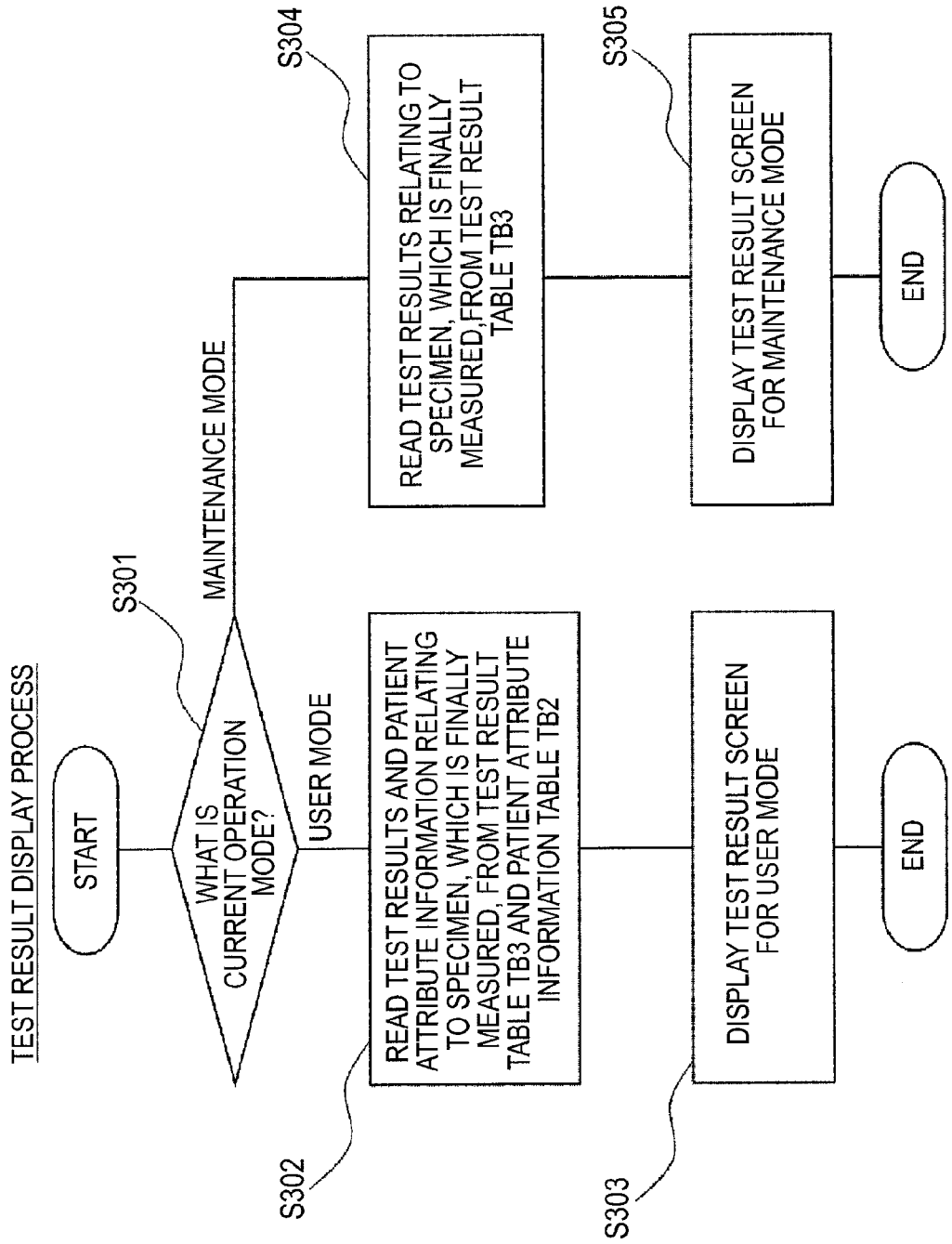
FIG. 13 is a flow chart illustrating a flow of a test result display process by the information processing unit of the specimen testing apparatus according to the embodiment.

FIG. 13 is a flow chart illustrating a flow of the test result display process by the information processing unit 5 of the specimen testing apparatus 1. The operator executes the operation of selecting the browser icon in the tool bar in the display screen in the case of viewing the test results in the past. With this operation, the test results in the past are read from the test result table TB3, and the browser screen including the test results is called up. When the CPU 51a receives the instruction to display such a browser screen, the CPU 51a executes the process in step S301.

The CPU 51a determines which one of the user mode and the maintenance mode the current operation mode of the specimen testing apparatus 1 is in (step S301). When the current operation mode is in the user mode (the "user mode" in step S301), the CPU 51a reads the test results of the specimen, which were most recently measured, from the test result table TB3, reads the patient attribute information, which contains the same patient ID as that in the test result, from the patient attribute information table TB2 (step S302), displays the test result screen (the browser screen) for the "user mode" on the image display section 52 (step S303), and terminates the process. On the other hand, when the current operation mode is in the "maintenance mode" in step S301, the CPU 51a reads the test results of the specimen, which were most recently measured, from the test result table TB3 (step S304), displays the test result screen (browser screen) for the "maintenance mode" on the image display section 52 (step S305), and terminates the process.

Figure 14:
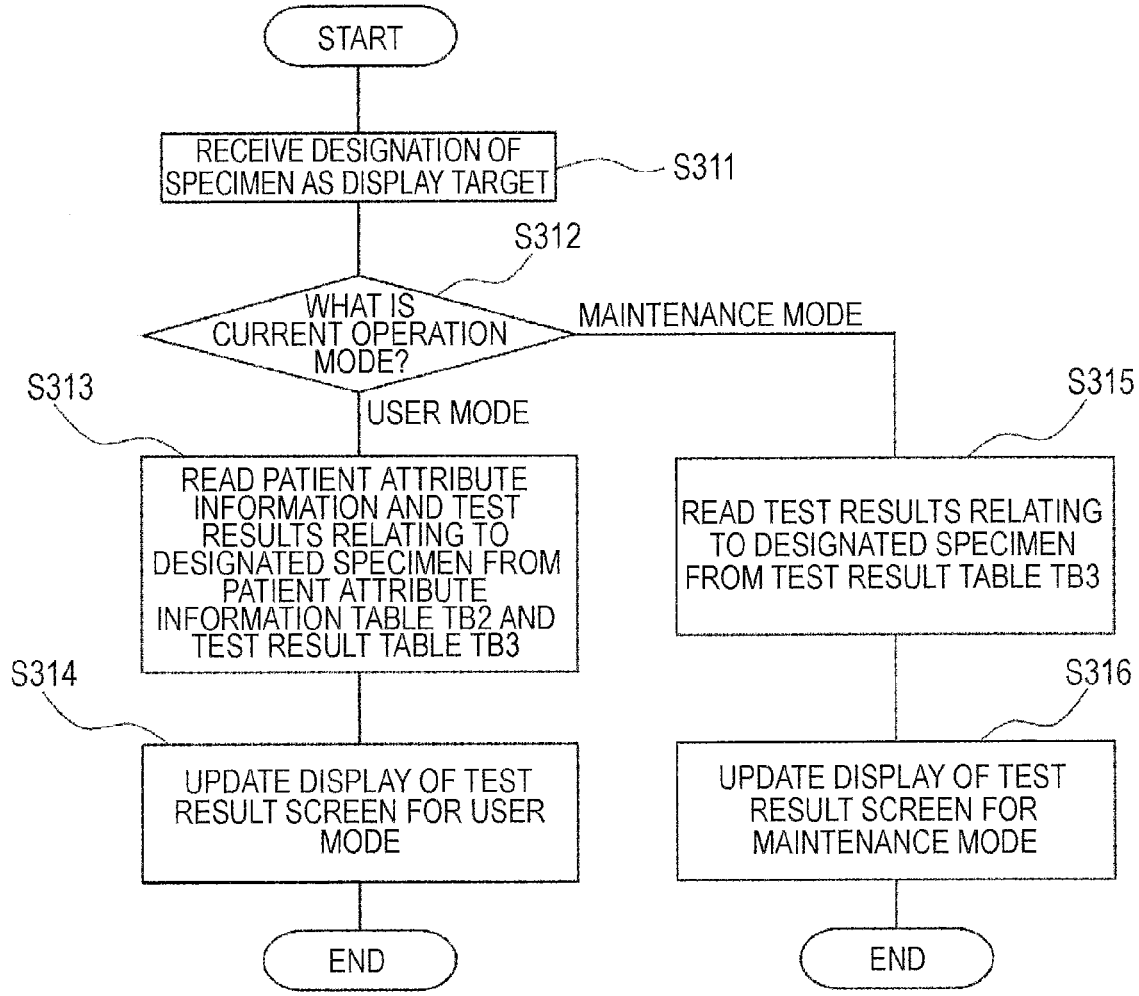
FIG. 14 is a flow chart illustrating a flow of a test result display switching process by the information processing unit of the specimen testing apparatus according to the embodiment.

FIG. 14 is a flow chart illustrating a flow of a test result display switching process by the information processing unit 5 of the specimen testing apparatus 1. It is possible to switch the display to the test results of another specimen in the state in which the test result screen is displayed as described above. In this case, the operator executes an operation of displaying a search screen for the test results, and can give a designation of a specimen as a display target to the specimen testing apparatus 1 by inputting the specimen ID or the like as a search key to instruct the searching or by selecting an "up" or "down" icon provided in the tool bar 813. When the CPU 51a receives the input regarding the specimen as the display target (step S311), the CPU 51a executes the process in step S312.

In step S312, the CPU 51a determines which one of the user mode and the maintenance mode the current operation mode of the specimen testing apparatus 1 is in (step S312). When the current operation mode is in the user mode (the "user mode" in step S312), the CPU 51a reads the test results of the designated specimen from the test result table TB3, reads the patient attribute information, which contains the same patient ID as that in the test result, from the patient attribute information table TB2 (step S313), displays the test result screen for the "user mode", which contains the read patient attribute information and the test result, on the image display section 52 (step S314), and terminates the process. On the other hand, when the current operation mode is in the "maintenance mode" in step S312, the CPU 51a reads the test results of the designated specimen from the test result table TB3 (step S315), displays the test result screen for the "maintenance mode", which contains the read test result, on the image display section 52 (step S316), and terminates the process.

In the test result display process, although the patient attribute information is displayed on the test result screen 810 for the user mode, the patient attribute information is not displayed on the test result screen 820 for the maintenance mode. With such a configuration, it is possible to prevent the maintenance technicians from viewing the patient attribute information.

<Test Result Storage Process>

Figure 15:
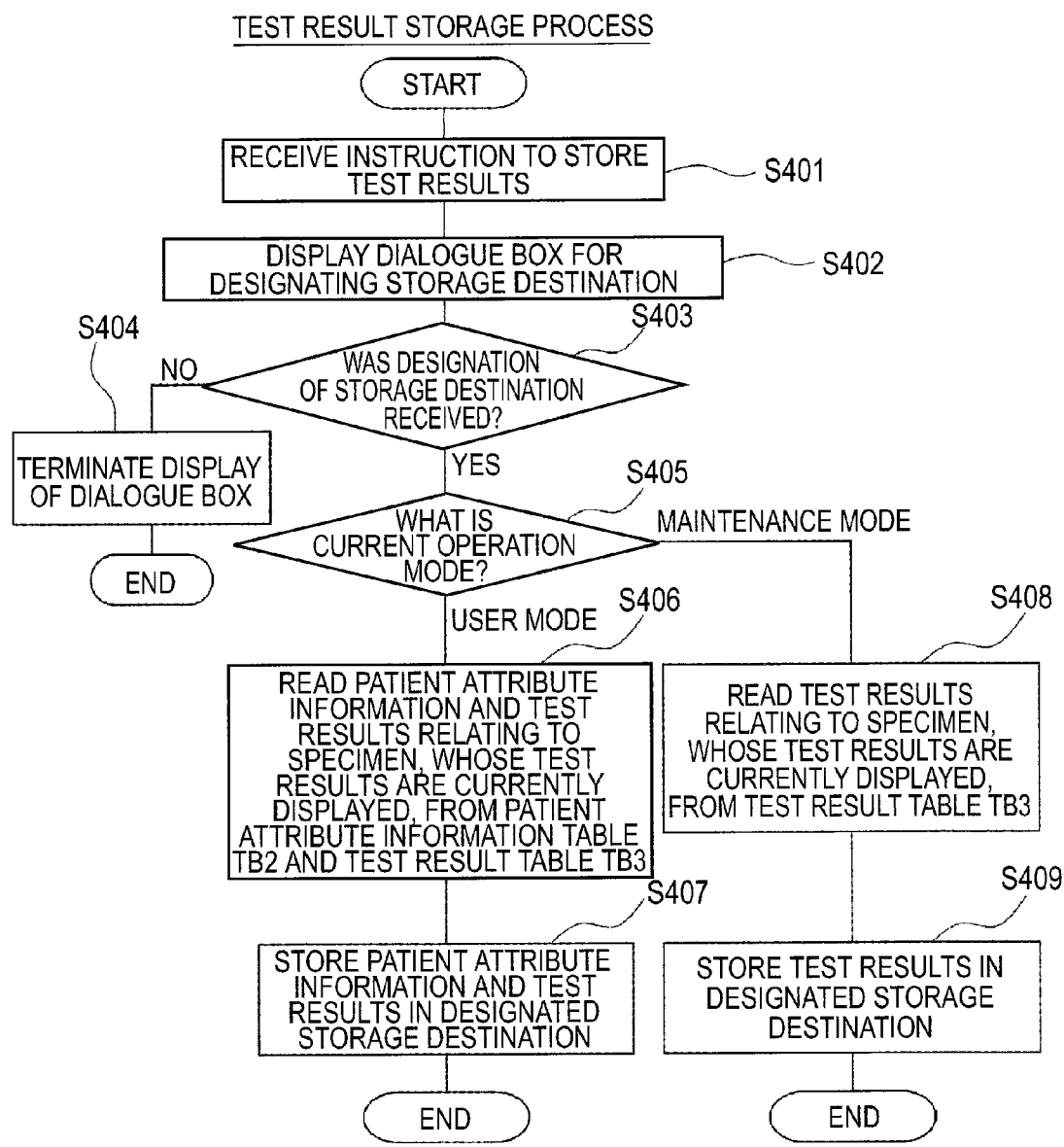
FIG. 15 is a flow chart illustrating a flow of a test result storage process by the information processing unit of the specimen testing apparatus according to the embodiment.

FIG. 15 is a flow chart illustrating a flow of a test result storage process by the information processing unit 5 of the specimen testing apparatus 1. It is possible to cause the external storage device 8 to store the test results of the specimen, whose test results are being displayed, in the state in which the test result screen is displayed as described above. The operator can give an instruction to store the test results to the specimen testing apparatus 1 by selecting the "data operation" menu provided in the menu bar 812 and selecting the "backup" item included in the displayed pull-down menus. When the CPU 51a receives the instruction to store the test results (step S401), the CPU 51a executes the process in step S402.

In step S402, the CPU 51a causes the image display section 52 to display a dialogue box (not shown) for designating a storage destination (step S402). An input area for designating a path of the storage destination for the test results is provided in this dialogue box, and the operator can designate the external storage device 8 as a storage destination by inputting a path of the external storage device 8 in this input area. In addition, a cancel button is included in this dialogue box, and the operator can terminate the display of the dialogue box by executing an operation of selecting this cancel button.

When the CPU 51a receives the selection of the cancel button (NO in step S403), the CPU 51a terminates the display of the dialogue box (step S404), and terminates the process. On the other hand, when the CPU 51a receives the designation of the path of the storage destination by the above-mentioned dialogue box (YES in step S403), the CPU 51a determines which one of the user mode and the maintenance mode the current operation mode of the specimen testing apparatus 1 is in (step S405), reads the test results of the specimen, whose test results are being displayed, from the test result table TB3 when the current operation mode is in the user mode (the "user mode" in step S405), reads the patient attribute information, which contains the same patient ID as that in the test results, from the patient attribute information table TB2 (step S406), stores the patient attribute information and the test results in the designated storage destination (step S407), and terminates the process. On the other hand, the CPU 51a reads the test results of the specimen from the test result table TB3 (step S408) when the current operation mode is in the "maintenance mode" in step S405, stores the test results in the designated storage destination (step S409), and terminates the process.

In the test result storage process, although the patient attribute information is stored in the storage destination along with the test results when the user mode has been set, not the patient attribute information but only the test results are stored when the maintenance mode has been set. With such a configuration, it is possible to prevent the maintenance technicians from viewing the patient attribute information.

<Test Result Printing and Transmitting Process>

Figure 16:
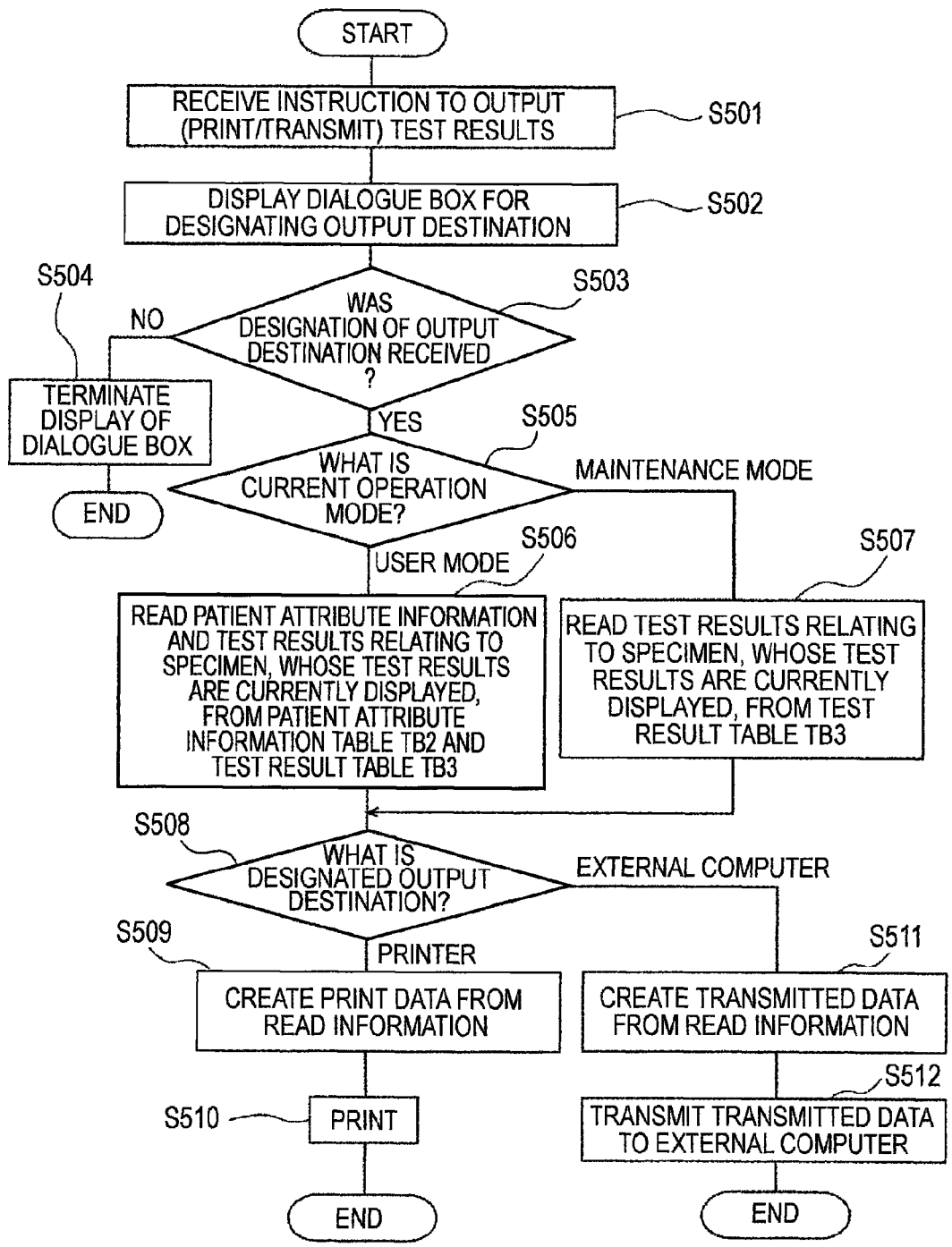
FIG. 16 is a flow chart illustrating a flow of a test result printing and transmitting process by the information processing unit of the specimen testing apparatus according to the embodiment.

FIG. 16 is a flow chart illustrating a flow of a test result printing and transmitting process by the information processing unit 5 of the specimen testing apparatus 1. It is possible to cause the printer 9 to print the test results of the specimen, whose test results are being displayed, or transmit them to the external computer 7 in the state in which the test result screen is displayed as described above. The operator can give an instruction to print or transmit the test results to the specimen testing apparatus 1 by executing an operation of selecting an "output" icon included in the tool bar 813. When the CPU 51a receives the instruction to output the test results (step S501), the CPU 51a executes the process in step S502.

In step S502, the CPU 51a causes the image display section 52 to display a dialogue box (not shown) for designating an output designation (step S502). It is possible to designate the printer 9 or the external computer 7 as the output destination of the test results by this dialogue box. In addition, a cancel button is included in this dialogue box, and the operator can terminate the display of the dialogue box by the operation of selecting this cancel button.

When the CPU 51a receives the selection of the cancel button (NO in step S503), the CPU 51a terminates the display of the dialogue box (step S504), and terminates the process. On the other hand, when the output destination is designated by the above-mentioned dialogue box (YES in step S503), the CPU 51a determines which one of the user mode and the maintenance mode the current operation mode of the specimen testing apparatus 1 is in (step S505), reads the test results of the specimen, whose test results are being displayed, from the test result table TB3 when the current operation mode is in the user mode (the "user mode" in step S505), and reads the patient attribute information, which contains the same patient ID as that in the test results, from the patient attribute information table TB2 (step S506). On the other hand, the CPU 51a reads the test results of the above-mentioned specimen from the test result table TB3 (step S507) when the current operation mode is in the "maintenance mode" in step S505.

The CPU 51a determines which one of the printer 9 and the external computer 7 is designated as the output destination (step S508), and generates print data in a page format to be printed from the read information (step S509) when the printer 9 has been designated as the output destination ("printer" in step S508). Here, since the patient attribute information and the test results have been read in the case of the user mode, the print data is created such that both the patient attribute information and the test results are printed. On the other hand, since not the patient attribute information but only the test results have been read in the case of the maintenance mode, the print data is created such that only the test results are printed. The CPU 51a transmits the thus created print data to the printer 9, executes a print process (step S510), and terminates the process.

On the other hand, when the external computer 7 is designated as the output destination in step S508 ("external computer" in step S508), the CPU 51a creates the transmitted data in a format to be transmitted from the read information (step S511). Here, since the patient attribute information and the test results have been read in the case of the user mode, the transmitted data is created so as to contain both the patient attribute information and the test results. On the other hand, since not the patient attribute information but only the test results have been read in the case of the maintenance mode, the transmitted data is created so as to contain only the test results. The CPU 51a transmits the thus created transmitted data to the external computer 7 (step S512) and terminates the process. The transmitted data is received by the external computer 7, and stored in the hard disk of the external computer 7.

In the test result printing and transmitting process, although the patient attribute information is printed by the printer 9 or transmitted to the external computer 7 along with the test results when the user mode has been set, only the test results are printed or transmitted to the external computer 7 when the maintenance mode has been set. With such a configuration, it is possible to prevent the maintenance technicians from viewing the patient attribute information.

[Operations of Test Information Management Apparatus 6]

Hereinafter, the description will be made of the operation of the test information management apparatus 6 according to this embodiment.

<Log-In Process>

Figure 17:
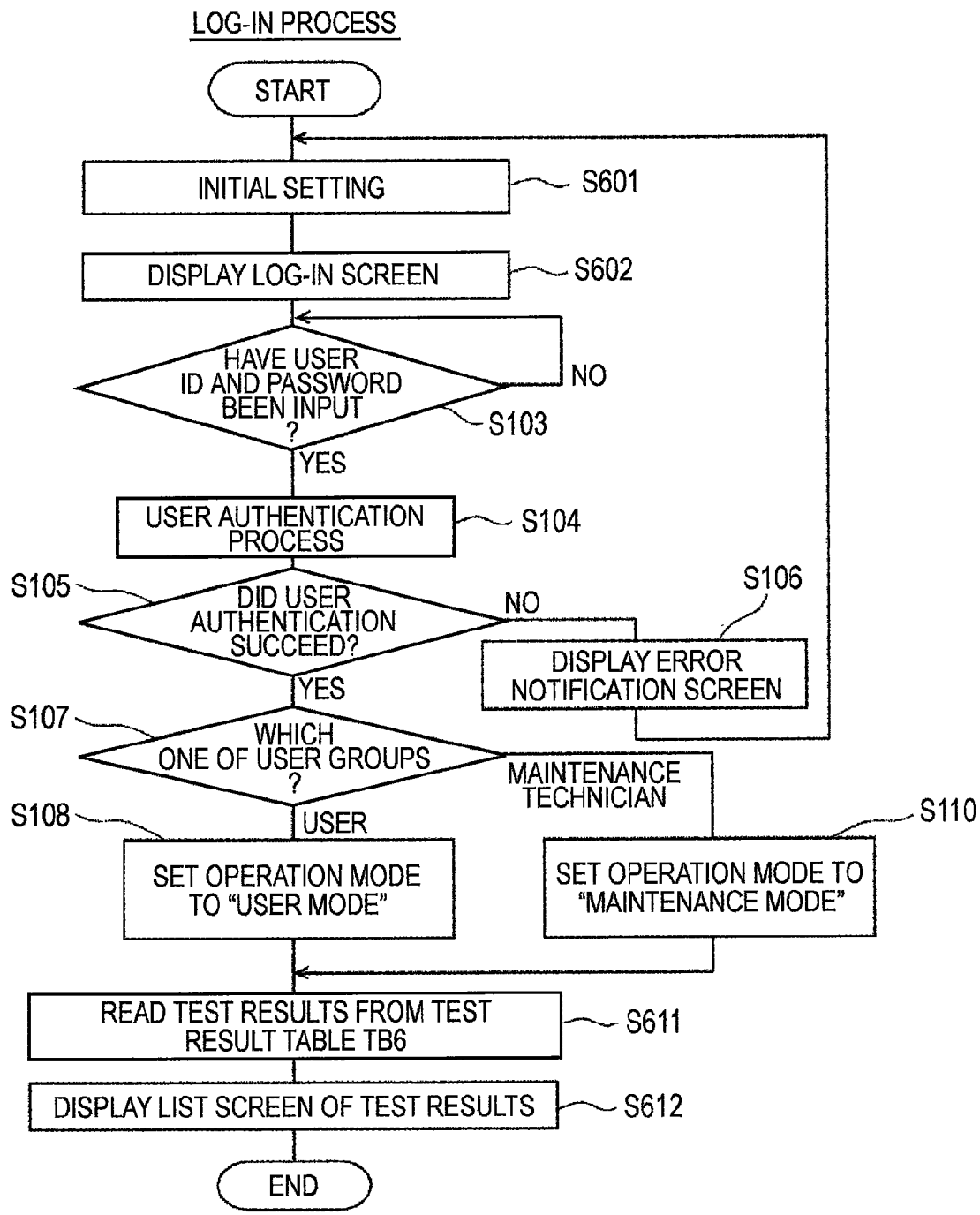
FIG. 17 is a flow chart illustrating a flow of a log-in process by the test information management apparatus according to the embodiment.

FIG. 17 is a flow chart illustrating a flow of a log-in process by the test information management apparatus 6. When the computer 6a is started, and the operator gives an instruction to execute the computer program 64a, the CPU 61a executes the initial setting of the program 64a (step S601) and displays a log-in screen on the image display section 62 (step S602). Input boxes for inputting the user ID and the password, respectively are provided in the log-in screen, and the operator inputs its own user ID and the password to the test information management apparatus 6 using an input section 63. The CPU 61a waits for the input of the user ID and the password (NO in step S603). When the CPU 61a receives the input of the user ID and the password (YES in step S603), the CPU 61a executes the user authentication process (step S604).

In the user authentication process, the CPU 61a checks the input user ID and the password with the user ID and the password registered in the user authentication table TB4 and determines whether the input user ID and the password are the ones which have been registered. When the user authentication fails (NO in step S605), the CPU 51a displays a screen for notifying the occurrence of the user authentication error (step S606) and then returns the process to step S602.

When the user authentication succeeds (YES in step S605), the CPU 61a confirms the operator group of the record including the user ID and the password in the user authentication table TB1 and determines which one of the "user" and the "maintenance technician" the operator group is in (step S607). When the operator group is in the "user" (the "user" in step S607), the CPU 61a sets the operation mode of the test information management apparatus 6 to the "user mode" (step S608). The operators belonging to the group of the "user" are authorized to output the patient attribute information. That is, the "user mode" is an operation mode of the test information management apparatus 6, in which it is possible to output the patient attribute information.

On the other hand, when the operation group is in the "maintenance technician" (the "maintenance technician" in step S607), the CPU 61a sets the operation mode of the test information management apparatus 6 to the "maintenance mode" (step S610). The operators belonging to the group of the "maintenance technician" are not authorized to output the patient attribute information. That is, the "maintenance mode" is an operation mode of the test information management apparatus 6, in which the output of the patient attribute information is limited. When the setting to the "user mode" or the "maintenance mode" is completed, the CPU 61a reads the information registered in the test result table TB6 (step S611), displays a list screen (not shown) of the test results on the image display section 62 (step S612), and terminates the process.

<Test Result Display Process>

Figure 18:
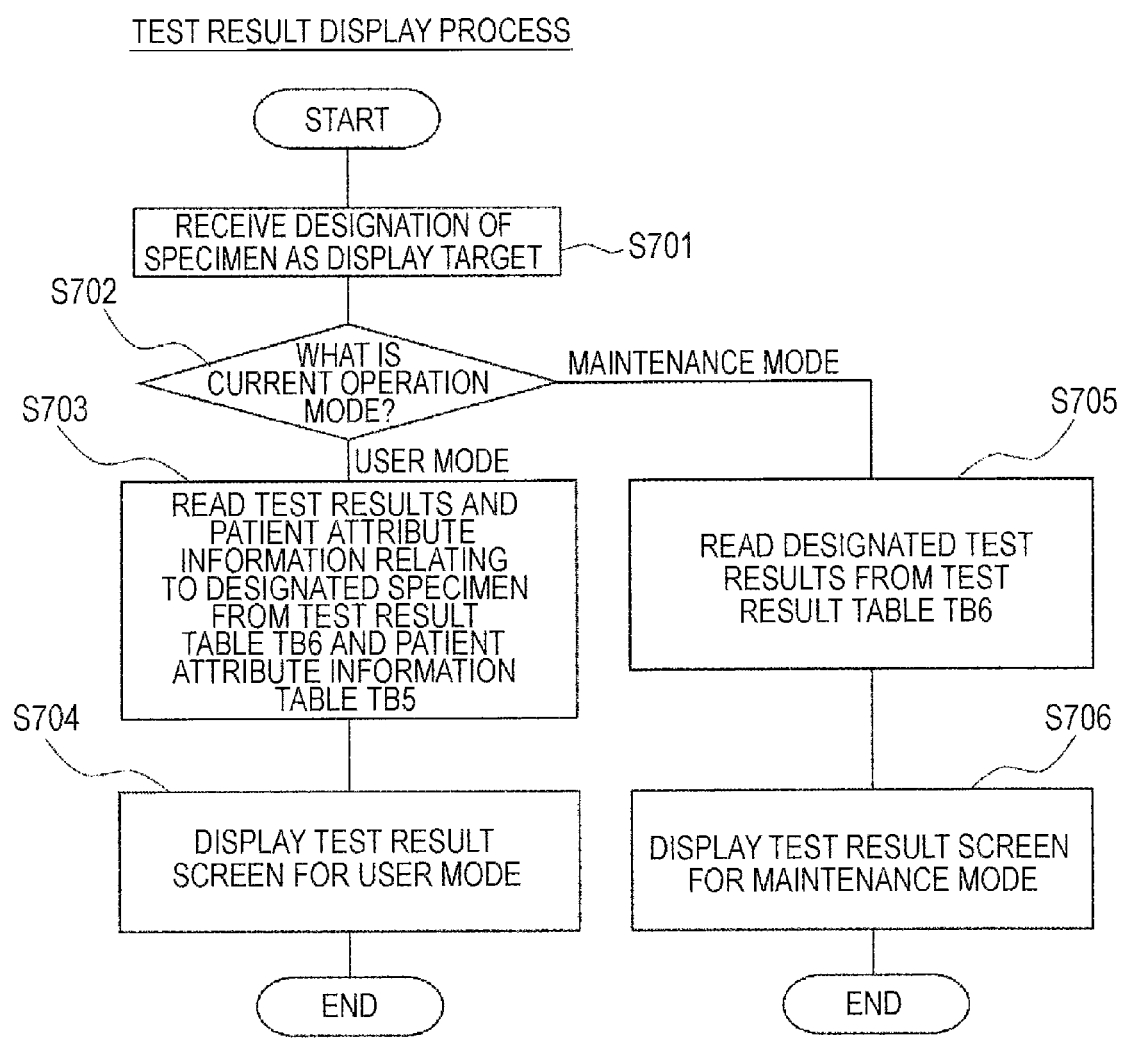
FIG. 18 is a flow chart illustrating a flow of a test result display process by the test information management apparatus according to the embodiment.

FIG. 18 is a flow chart illustrating a flow of a test result display process by the test information management apparatus 6. The test result list screen is a screen which displays in a list format the specimen ID and the test results for each specimen, and it is possible to display the test result screen of a specimen by performing a selecting operation such as a double-clicking of the test results of the specimen to be displayed using a mouse when the detailed test results are to be displayed. The operator performs an operation of designating a specimen, whose test results are to be displayed, as described above when viewing the detailed test results in the past by the specimen testing apparatus 1. When the CPU 61a receives the input regarding the specimen to be displayed, the CPU 61a executes the process in step S701.

In step S701, the CPU 61a determines which one of the user mode and the maintenance mode the current operation mode of the test information management apparatus 6 is in (step S701), reads the test results of the designated specimen from the test results table TB3 when the current operation mode is in the user mode (the "user mode" in step S701), reads the patient attribute information, which contains the same patient ID as that in the test results, from the patient attribute information table TB2 (step S702), displays the test result screen for the "user mode", which contains the read patient attribute information and test results, on the image display section 62 (step S703), and terminates the process. On the other hand, the CPU 61a reads the test results of the designated specimen from the test result table TB6 (step S704) when the current operation mode is in the "maintenance mode" in step S701, displays the test result screen for the "maintenance mode", which contains the read test results on the image display section 62 (step S705), and terminates the process.

The operations of the test information management apparatus 6 in the case of switching the display of the test result screen to the test results for another specimen, in the case of storing the test results in the external storage device 8, and in the case of printing the test results or transmitting the test results to the external computer 7 are the same as those of the information processing unit 5 of the specimen testing apparatus 1 as described above. Accordingly, the description thereof will be omitted.

Other Embodiments

Although the description has been made of a configuration in which the test results screen including the patient attribute information along with the test results was displayed in the user mode in the above-mentioned embodiment, it is also applicable that the configuration is made such that each user can set in advance the patient attribute information to be excluded from the display targets in the test result screen for the user mode. That is, the user sets in advance in the information processing unit 5 the items, which are to be excluded from the display targets, from among the items of the patient attribute information, and stores the items, which are to be excluded, in the hard disk 51*d* correspondingly to the user ID. It is also applicable that the configuration is made such that the test result screen including the test results and the patient attribute information of the items other than the items to be excluded in the patient attribute information is created and displayed when the test results are displayed. At this time, it is also possible that the configuration is made such that the name of the patient cannot be set as a target to be excluded. The same is true of the output formats other than displaying (storage, printing, and transmitting).

In addition, although the description has been made of the configuration in which the test result screen including the test results without including the patient attribute information was displayed in the maintenance mode in the above-mentioned embodiment, the present invention is not limited thereto. For example, it is also applicable that the configuration is made such that the test results, which do not contain only the attribute information, with which a patient can be specified, such as a name of a patient, and which contain the other attribute information, is displayed in the maintenance mode. It is also applicable that the configuration is made such that a user sets in advance the items, for which displaying is to be restricted, from among the patient attribute information in the test result screen for the maintenance mode, and generates and displays the test result screen including the test results and the patient attribute information of the items other than the target items, for which displaying is to be restricted, from among the patient attribute information when the test results are displayed. In addition, it is also applicable that the configuration at this time is made such that the names of the patients are fixedly set as a target item for which displaying is always to be restricted and cannot be set as a display target. The same is true of the output formats other than displaying.

In addition, it is also applicable that the configuration is made such that assisting information for assisting the test results is displayed along with the test results in the test result screen in the maintenance mode in order that the maintenance technician can determine malfunctioning or the necessity of maintenance (the replacement of parts, the cleaning of members, the changing of setting values, and the like) of the apparatus. For example, it is also applicable that the configuration is made such that the coordinate value of a gravity center position of respective clusters in a scattergram is displayed along with the scattergram in order to determine whether the scattergram is normal, such that sensitivity information of a signal used for a histogram is displayed along with the histogram, or such that the temperature, the sensitivity, the clogging level, the sampling number, and the like of the detecting section are displayed along with the numerical data of PLT.

Although the description has been made of the configuration in which the patient attribute information is not displayed at all in the test result screen for the maintenance mode in the above-mentioned embodiment, the present invention is not limited thereto. It is also applicable that the configuration is made such that the patient attribute information, which is necessary to determine whether the specimen testing apparatus 1 functions normally, is displayed in the test result screen for the maintenance mode, and the other information is not displayed. As for a blood cell analysis apparatus, since criteria for positive/negative determination are different for the same test item depending on age and sex, it is applicable that the configuration is made such that the age and sex from among the patient attribute information are displayed even in the test result screen for the maintenance mode. As for a urinary sediment analyzer, since criteria for positive/negative determination are different for RBC, SPERM (sperm), and the like depending on the sex, age, and diagnosis and treatment departments (medical wards), it is applicable that the configuration is made such that the age, the sex, and the diagnosis and treatment departments from among the patient attribute information are displayed even in the test result screen for the maintenance mode. The same is true of the output formats other than displaying.

Although the description has been made of the configuration in which nothing is displayed in the patient attribute information display part 814*d* in the test result screen 820 for the maintenance mode in the above-mentioned embodiment, the present invention is not limited thereto. It is also applicable that the configuration is made such that a text, which indicates that the displaying of the patient attribute information is limited, instead of the patient attribute information is displayed in the patient attribute information display part 814*d* in the test result screen 820 for the maintenance mode, or such that the text, which indicates that the maintenance mode is currently set, is displayed. In addition, it is also applicable that the configuration is made such that the above-mentioned assisting information for assisting the test results instead of the patient attribute information is displayed in this patient attribute display part 814*d*.

Although the description has been made of the configuration in which the user authentication table for storing the user IDs, the passwords, and the operator group while making a correspondence between them is used in order to authenticate the operators in the above-mentioned embodiment, the present invention is not limited thereto. For example, it is also applicable that the configuration is made such that a character (or a character string) for specifying the type of operator is included in the user ID, and the type of operator is determined by recognizing the character (or the character string) included in the input user ID. In addition, another configuration is also applicable in which it is determined that the operator is one of the types of the user or the maintenance technician when the user ID includes a specific character (or a character string), and it is determined that the operator is the other type when the user ID does not include the specific character (or the character string). Specifically, a user ID to be allocated to a maintenance technician is set so as to include a specific character (or a character string) for specifying a maintenance technician. When the operator is authenticated, it is determined whether or not the specific character (or the character string) for specifying a maintenance technician is included in the input user ID. The configuration is applicable in which the operator logs-in the maintenance mode after the authentication of the password when it is determined that the specific character (or the character string) is included in the user ID, and the operator logs-in the user mode after the authentication of the password when it is determined that the specific character (or the character string) is not included in the user ID.

Although the description has been made of the case in which the specimen testing apparatus 1 is a multi-item blood cell analyzing apparatus in the above-mentioned embodiment, the present invention is not limited thereto. It is also applied to a specimen testing apparatus other than the multi-item blood cell analyzing apparatus, such as a blood coagulation measurement apparatus, an immuno-analytical equipment, a urinary sediment analyzer, or a urine qualitative analyzer.

In addition, although the description has been made of the configuration in which all the processes in the computer program 54a are executed by a single computer 5a in the above-mentioned embodiment, the present invention is not limited thereto. A distributed system is also applicable in which the same processes as those in the above-mentioned computer program 54a are distributed to and executed by a plurality of apparatuses (computers).

In addition, although the description has been made of the configuration in which all the processes in the computer program 64a are executed by a single computer 6a in the above-mentioned embodiment, the present invention is not limited thereto. A distributed system is also applicable in which the same processes as those in the above-mentioned computer program 64a are distributed to and executed by a plurality of apparatuses (computers).

The specimen testing apparatus according to the present invention is useful as a specimen testing apparatus such as a multi-item blood cell analyzing apparatus, a blood coagulation measurement apparatus, an immuno-analytical equipment, a urinary sediment analyzer, or a urine qualitative analyzer. In addition, the test information management apparatus according to the present invention is useful as an LIS (Laboratory Information System). Moreover, the test information output method according to the present invention is useful as an output method for test information by a specimen testing apparatus as described above.

What is claimed is:

1. A specimen testing apparatus comprising:
a testing section for testing a specimen;
a storage section for storing subject attribute information and test results in correspondence with each other, the subject attribute information comprising attribute information with which a subject from which the specimen has been collected can be specified, and the test results being obtained by testing the specimen collected from the subject relating to the subject attribute information by the testing section;
an output section for outputting information stored in the storage section; and
a controller, wherein
the controller:
receives input of the subject attribute information;
controls the testing section such that the testing section tests the specimen and obtains the test results;
causes the storage section to store the subject attribute information and the test results of the specimen collected from the subject relating to the subject attribute information in correspondence with each other;
receives from an operator, identification information for identifying the operator; and
controls the output section to output first test information comprising the subject attribute information and the test results relating to the subject attribute information when the received identification information corresponds to first type information which indicates that the operator belongs to the first type, and controls the output section to output second test information comprising not the attribute information, with which the subject can be specified, from among the subject attribute information, but the test results relating to the subject attribute information when the received identification information corresponds to second type information which indicates that the operator belongs to the second type.

2. The specimen testing apparatus of claim 1, wherein
the storage section stores the identification information and, the first type information or the second type information in correspondence with each other.

3. The specimen testing apparatus of claim 1, wherein
the subject attribute information comprises a first item relating to the attribute information with which a subject can be specified and a second item relating to other attribute information of the subject, and
the first test information comprises the first item of the subject attribute information stored in the storage section, and the test results relating to the subject attribute information.

4. The specimen testing apparatus of claim 3, wherein
the controller further receives setting of an item of the subject attribute information, the item being to be excluded from targets output from the output section, when the received identification information corresponds to the first type information, and
the first test information comprises both the information of the item other than the excluded item from among the subject attribute information stored in the storage section and the test results relating to the subject attribute information when the excluded item has been set, and the received identification information corresponds to the first type information.

5. The specimen testing apparatus of claim 1, wherein
the subject attribute information comprises an item relating to the attribute information with which a subject can be specified and an item relating to other attribute information of the subject,
the controller receives setting of the item of the subject attribute information, for which the output is to be restricted when the received identification information corresponds to the second type information, and
the second test information comprises not the item set as item for which the output is restricted, and item relating to the attribute information, with which a subject can be specified, from among the subject attribute information stored in the storage section, but the test results relating to the subject attribute information when the received identification information corresponds to the second type information.

6. The specimen testing apparatus of claim 5, wherein
the subject attribute information comprises a name of a subject as the attribute information with which the subject can be specified, and
the item for which the output is restricted when the received identification information corresponds to the second type information always comprises the item of the subject's name.

7. The specimen testing apparatus of claim 1, wherein
the output section comprises a display, and
the output of the first and second test information is executed by displaying on the display.

8. The specimen testing apparatus of claim 7, wherein
the display is capable of displaying a test result screen including a first area for displaying the subject attribute information and a second area for displaying the test results,
the controller
causes the display to display the test result screen containing the subject attribute information, which is stored in the storage section, in the first area and the test results relating to the subject attribute information in the second area when the received identification information corresponds to the first type information; and causes the display to display the test result screen containing not the attribute information, with which a subject can be specified from among the subject attribute information stored in the storage section, in the first area, but the test results relating to the subject attribute information in the second area when the received identification information corresponds to the second type information.

9. The specimen testing apparatus of claim 8, wherein the controller causes the display to display the test result screen including assisting information for assisting the test result in the second area in addition to the test result when the received identification information corresponds to the second type information.

10. The specimen testing apparatus of claim 1, further comprising an interface to which an external storage medium is detachably connected, wherein
the controller writes the second testing information in the external storage medium connected to the interface according to operation by the operator when the received identification information corresponds to the second type information.

11. The specimen testing apparatus of claim 1, wherein the controller is capable of communicating with an external computer, and
the controller transmits the second test information to the external computer according to operation by the operator when the received identification information corresponds to the second type information.

12. The specimen testing apparatus of claim 1, wherein the storage section stores both the subject attribute information containing age and sex and the results of a blood cell count test as the test results, and
the controller causes the output section to output the second test information comprising not the information other than the age and sex from among the subject attribute information stored in the storage section but the test results relating to the subject attribute information when the received identification information corresponds to the second type information.

13. The specimen testing apparatus of claim 1, wherein the storage section stores both the subject attribute information containing age, sex, a diagnosis and treatment department to which the subject belongs and the results of a urinary sediment test as the test results, and
the controller causes the output section to output the second test information containing not the information other than the age, sex, and the diagnosis and treatment department from among the subject attribute information stored in the storage section, but the test results relating to the subject attribute information when the received identification information corresponds to the second type information.

14. The specimen testing apparatus of claim 1, wherein the controller
causes the output section to output the first test information when the received identification information corresponds to the first type information which indicates that the operator is a user who uses the specimen testing apparatus, and
causes the output section to output the second test information when the received identification information corresponds to the second type information which indicates that the operator is a maintenance technician who executes maintenance of the specimen testing apparatus.

15. A specimen testing apparatus comprising:
a testing section for testing a specimen; and
a controller, including a storage section under control of a processor, the storage section storing instructions enabling the processor to carry out operations, comprising:
a step of receiving an input of subject attribute information including attribute information with which a subject from which the specimen has been corrected can be specified;
a step of obtaining test results by testing the specimen by the testing section;
a step of storing in the storage section the subject attribute information and the test results of the specimen collected from the subject relating to the subject attribute information in correspondence with each other;
a step of receiving from an operator, identification information for identifying the operator;
a first output step of outputting first test information comprising the subject attribute information stored in the storage section and the test results relating to the subject attribute information when the received identification information corresponds to first type information which indicates that the operator belongs to a first type; and
a second output step of outputting second test information comprising not the attribute information with which a subject can be specified from among the subject attribute information stored in the storage section, but the test results relating to the subject attribute information when the received identification information corresponds to second type information which indicates that the operator belongs to a second type.

16. A test information management apparatus comprising:
a storage section for storing subject attribute information and test result of a specimen in correspondence with each other, the subject attribute information comprising attribute information with which a subject from which a specimen has been collected can be specified, and the test result being obtained from the specimen collected from the subject relating to the subject attribute information;
an output section for outputting information stored in the storage section; and
a controller;
wherein the controller:
receives from an operator an input of identification information relating to the operator; and
causes the output section to output first test information comprising the subject attribute information stored in the storage section and the test results relating to the subject attribute information when the received identification information corresponds to first type information which indicates that the operator belongs to the first type, and causes the output section to output second test information comprising not the attribute information, with which the subject can be specified, from among the subject attribute information stored in the storage section, but the test results relating to the subject attribute information when the received identification information corresponds to second type information which indicates that the operator belongs to the second type.

* * * * *